United States Patent
Weller et al.

(10) Patent No.: US 7,531,575 B2
(45) Date of Patent: May 12, 2009

(54) METHOD OF MODULATING CELLULAR ACTIVITY AND AGENTS USEFUL FOR SAME

(75) Inventors: Michael Weller, Gomaringen (DE); Wolfgang Wick, Tübingen (DE); Jörg Wischhusen, Tübingen (DE); Michael Platten, Hamburg (DE)

(73) Assignee: Eberhard-Karls-Universität Tübingin, Tübigen (DE)

( * ) Notice: Subject to any disclaimer, the term of this patent is extended or adjusted under 35 U.S.C. 154(b) by 1186 days.

(21) Appl. No.: 10/697,655

(22) Filed: Oct. 31, 2003

(65) Prior Publication Data

US 2008/0103204 A1    May 1, 2008

Related U.S. Application Data

(60) Provisional application No. 60/422,504, filed on Oct. 31, 2002.

(51) Int. Cl.
*A61K 31/195* (2006.01)
*A61K 43/00* (2006.01)

(52) U.S. Cl. ........................ 514/563; 514/903

(58) Field of Classification Search ............... 514/563, 514/903
See application file for complete search history.

(56) References Cited

U.S. PATENT DOCUMENTS

| 6,127,393 | A | 10/2000 | Fernandez |
| 6,407,125 | B1 | 6/2002 | Fernandez |
| 6,407,139 | B1 | 6/2002 | Isaji |
| 2002/0128290 | A1 | 9/2002 | Ohshima |
| 2005/0239892 | A1 | 10/2005 | Meydani |

FOREIGN PATENT DOCUMENTS

| CA | 2 495 592 | 3/2004 |
| EP | 1369114 | 6/2002 |
| JP | 2003-026575 | 1/2003 |
| JP | 2005-089345 | 9/2003 |
| WO | 2006/053390 | 5/2006 |

OTHER PUBLICATIONS

Tamai, Hideo, et al. "Impact of tranilast on restenosis after coronary angioplasty: Tranilast Restenosis Following Angioplasty Trial (TREAT)," American Heart Journal, 138(5), 1999, 968-975.*
Rock, R. Bryan et al. "Microglia as a Pharmacological Target in Infectious and Inflammatory Diseases of the Brain," J. Neuroimmune Pharmacol, 1, 2006, 117-126.*
Loscher, Wolfgang et al. "Drug resistance in brain diseases and the role of drug efflux transporters," Neuroscience, 6, 2005, 591-602.*
Zappulla et al. "Mast cells: new targets for multiple sclerosis therapy?" Journal of Neuroimmunology, 2002, 131, 5-20.*
Platten, Michael; et al., "N-[3,4-dimethoxycinnamoyl]-anthranilic acid (tranilast) suppresses microglial inducible nitric oxide synthase (iNOS) expression and activity induced by interferon-gama (IFN-gama)", British Journal of Pharmacology, 2001, 134:1279-84.
Azuma, H. et al. (1976) "Pharmacological properties of N-(3', 4'-dimethoxycinnamoyl) anthranilic acid (N-5'), a new anti-atopic agent." Br. J. Pharmac.58: 483-488.
Fallarino, F.; et al, "T cell apoptosis by tryptophan catabolism", Cell Death and Differentiation, 2002, 9 (10):1069-1077.
Moffett, Jr et al. (2003) "Tryptophan and the immune response" Immunology and Cell Biology 81(4):247-265.
Platten, M. et al (2005) "Treatment of autoimmune neuroinflammation with a synthetic tryptophan metabolite." Science 310:850-855.
Shigeki, S et al. (1997) "Treatment of Keloid and Hypertrophic scares by iontophoretic transdermal delivery of tranilast." Scan J. Reconstr Hand Surg. 31(2):151-158.
Terness, P.; et al, "Inhibition of allogeneic T cell proliferation by indoleamine-2, 3-dioxygenase-expressing dentritic cells: Mediation of suppression by tryptophan metabolites", Journal of Experimental Medicine, Aug. 19, 2002, 196 (4):447-457.
Widner, B., et al, "Tryptophan degradation to control T-cell responsiveness", Immunology Today, May 2000, 21 (5):250.
Wirleitner, B., et al., "Interferon-gamma-induced conversion of tryptophan: immunologic and neuropsychiatric aspects", Current Medicinal Chemistry, 2003, 10(16):1581-1591.

* cited by examiner

*Primary Examiner*—Sharmila Gollamudi Landau
*Assistant Examiner*—Kortney L Klinkel
(74) *Attorney, Agent, or Firm*—Bozicevic, Field & Francis LLP; Pamela J. Sherwood

(57) ABSTRACT

Described is a rational design of therapeutic and/or prophylactic methods of treating conditions characterized by aberrant or otherwise unwanted microglial cell functioning and rational design methods for treating a range of neurological disorders which are characterized by nitric oxide induced neuronal damage.

9 Claims, 8 Drawing Sheets

A

B

METHOD OF MODULATING CELLULAR ACTIVITY AND AGENTS USEFUL FOR SAME

FIELD OF THE INVENTION

The present invention relates generally to a method of modulating microglial cell functional activity and to agents useful for same. More particularly, the present invention contemplates a method of downregulating microglial cell functional activity. The method of the present invention is useful, inter alia, in the treatment and/or prophylaxis of conditions characterised by aberrant, unwanted or otherwise inappropriate microglial cell functioning such as, but not limited to, diseases characterised by inappropriate nitric oxide production.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that prior art forms part of the common general knowledge in Australia.

Microglial cells share many morphological and functional features with monocytes and microphages and are thought to contribute to inflammatory processes in the brain. Microglia are activated during brain ischaemia, infection, demyelination, neurodegeneration and tumorigenesis (Gonzalez-Scarano, F. and Baltuch, G. 1999. *Annu Rev Neurosci*, 22:219-240). On a cellular level, activation of microglial cells, like monocytic cells, results in the expression of pro-inflammatory mediators such as cyclo-oxygenase type 2 (COX-2), tumour necrosis factor-$\alpha$ (TNF-$\alpha$) and nitric oxide (NO). NO is a free radical generated from -arginine by NO synthases (NOS) (Griffith, O. W. and Stuehr, D. J., 1995. *Annu Rev Physiol.*, 5:707-736). It is involved in a wide range of physiological and pathological processes including the regulation of vascular homeostasis, neurotransmission and inflammation (Nathan, C. 1992. *FASEB. J*, 6:3051-3064). Three isoforms of NOS have been characterized. Neuronal (type I or nNOS and endothelial) (type III or eNOS) NOS are constitutively expressed and are mainly regulating posttranscriptionally by calmodulin-dependent pathways. The inducible NOS isoform (type II or iNOS) is not expressed in healthy tissues but is rapidly expressed de novo in many cell types including astrocytes and microglia in response to lipopolysaccharide (LPS), a bacterial wall component, or inflammatory cytokines such as interleukin-1$\beta$ (IL-1$\beta$), TNF-$\alpha$ or IFN-$\gamma$ (Galea, E., Feinstein, D. L., and Reis, D. J., 1992. *Proc. Natl. Acad. Sci. USA.*, 89:10945-10949; Hu, S., Sheno, W. S., Peterson, P. K. and Chao, C. C., 1995. *Glia.*, 15:491-494; Nathan, C. and Xie, Q. W., 1994. *J. Biol. Chem.*, 269:13725-13728). When produced in excess amounts NO may promote neuronal death by reacting with superoxide anion to generate peroxynitrite (Beckman, J. S., Beckman, T. W., Chen, J., Marshall, P. A. and Freeman, B. A., 1990. *Prac. Natl. Acad. Sci. USA.*, 87:1620-1624). Consequently, overproduction of nitric oxide has been implicated in neurological disorders associated with neuronal damage including brain ischaemia, Parkinson's disease, Alzheimer's disease and amyotrophic lateral sclerosis (ALS) (Chabrier, P. E., Demerle-Pallardy, C. and Auguet, M. 1999, *Cell. Molecule. Life Sci.*, 55:1029-1035).

Accordingly, in light of the severe and debilitating outcome associated with the development of neurological disorders, and the apparent increase in the instance of onset thereof, there is an urgent need to develop methods of therapeutically and/or prophylactically treating these disorders either in the form of adjunctive therapies to currently utilised treatments or as a replacement to some of the currently available medications and/or methods of treatment.

In work leading up to the present invention, the inventors have determined that compounds of formula (I):

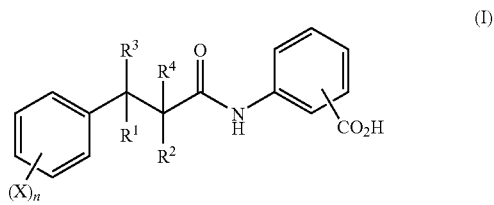

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, downregulate iNOS expression and activity in microglial cells. Without limiting the present invention in any way, in light of the downstream production of nitric oxide which occurs subsequently to iNOS expression, these findings provide a means of downregulating nitric oxide over production and thereby a means of treating neurological disorders which are characterised by nitric oxide induced neuronal damage. The identification of this activity now permits the rational design of therapeutic and/or prophylactic regimes for modulating microglial cell functioning and, in particular, for downregulating endothelial cell iNOS expression.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

One aspect of the present invention provides a method of downregulating microglial cell functional activity, said method comprising contacting said cell with an effective amount of a compound of formula (I) or a pharmaceutically acceptable salt thereof:

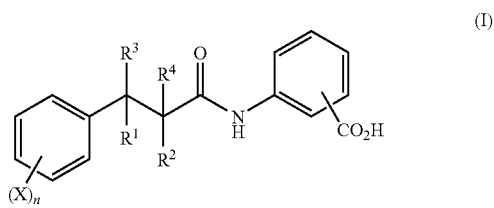

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3 for a time and under conditions sufficient to inhibit, retard or otherwise downregulate iNOS expression.

Another aspect of the present invention provides a method of downregulating microglial cell nitric oxide synthesis, said method comprising contacting said cell with an effective amount of a compound of formula (I) or a pharmaceutically acceptable salt thereof:

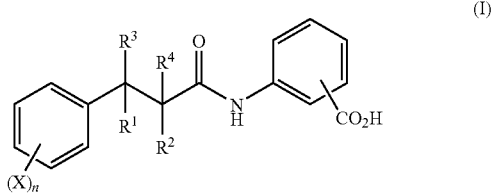

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to inhibit, retard or otherwise downregulate iNOS expression.

Yet another aspect of the present invention provides a method of down-regulating inflammatory cytokine-induced microglial cell functional activity, said method comprising contacting said cell with an effective amount of a compound of formula (I) or a pharmaceutically acceptable salt thereof:

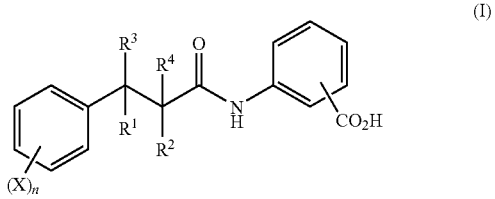

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to inhibit, retard or otherwise downregulate iNOS expression.

Still yet another aspect of the present invention provides a method of down-regulating interferon-γ-induced microglial cell functional activity, said method comprising contacting said cell with an effective amount of a compound of formula (I) or a pharmaceutically acceptable salt thereof:

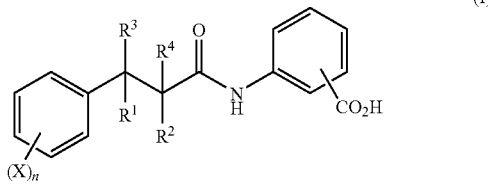

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to inhibit, retard or otherwise downregulate iNOS expression.

According to this preferred embodiment there is provided a method of down-regulating lipopolysaccharide-induced microglial cell functional activity, said method comprising contacting said cell with an effective amount of a compound of formula (I) or a pharmaceutically acceptable salt thereof for a time and under conditions sufficient to inhibit, retard or otherwise downregulate iNOS expression.

Preferably, said compound of formula (I) is 2-[[3-(3,4-dimethoxyphenyl)-1-oxo-2-propenyl]amino]benzoic acid.

Most preferably, said functional activity is nitric oxide synthesis.

Without limiting the present invention to any one theory or mode of action, "lipopolysaccharide" describes any of a group of related, 10 kDa, structurally complex components of the outer leaflet of the outer membrane of Gram-negative bacteria. Lipopolysaccharide molecules consist of three covalently linked regions: lipid A, core oligosaccharide, and an O side chain. The innermost layer, lipid A, which is responsible for the toxicity of the lipopolysaccharide, consists of six fatty acyl chains (sometimes hydroxylated) linked in various ways to two glucosamine residues. The branched core oligosaccharide contains ten saccharide residues, several of them unusual, and has a structure that appears to be similar in closely related bacterial strains. The outermost O side chain, which is highly variable and determines the antigenic specificity of the organism, is made up of many (≈50) repeating units of a branched tetrasaccharide containing further unusual sugar residues.

A further aspect of the present invention provides a method of downregulating microglial cell functional activity in a mammal, said method comprising administering to said mammal an effective amount of a compound of formula (I) or a pharmaceutically acceptable salt thereof:

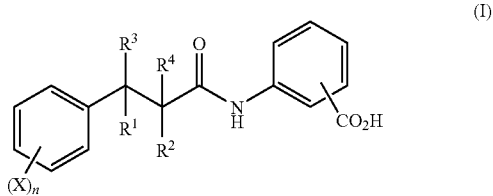

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to inhibit, retard or otherwise downregulate iNOS expression.

Another further aspect of the present invention provides a method of down-regulating inflammatory cytokine-induced microglial cell nitric oxide synthesis in a mammal, said method comprising administering to said mammal an effective amount of a compound of formula (I) or a pharmaceutically acceptable salt thereof:

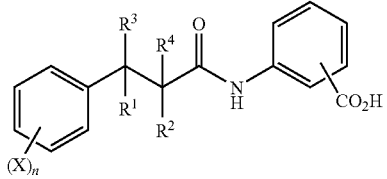

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to inhibit, retard or otherwise downregulate iNOS expression.

Still another further aspect of the present invention provides a method of down-regulating interferon-γ-induced microglial cell nitric oxide synthesis in a mammal, said method comprising administering to said mammal an effective amount of a compound formula (I) or a pharmaceutically acceptable salt thereof:

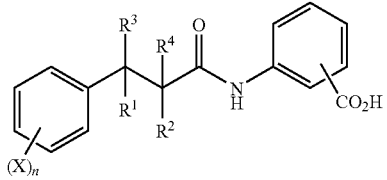

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to inhibit, retard or otherwise downregulate iNOS expression.

In another preferred embodiment, there is provided a method of down-regulating lipopolysaccharide-induced microglial cell nitric oxide synthesis in a mammal, said method comprising administering to said mammal an effective amount of a compound of formula (I) or a pharmaceutically acceptable salt thereof for a time and under conditions sufficient to inhibit, retard or otherwise downregulate iNOS expression.

Yet another further aspect of the present invention provides a method of upregulating microglial cell inhibited functional activity in a mammal, said method comprising administering to said mammal an effective amount of an antagonist of a compound of formula (I) or a pharmaceutically acceptable salt thereof:

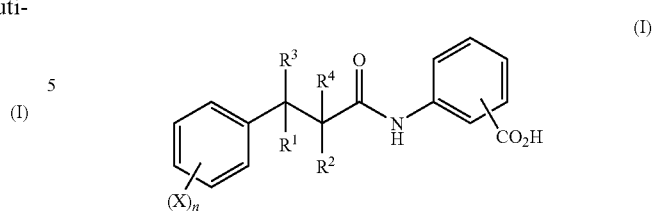

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to upregulate iNOS expression.

Another aspect of the present invention contemplates a method for the treatment and/or prophylaxis of a condition characterised by aberrant, unwanted or otherwise inappropriate microglial cell functional activity in a mammal, said method comprising administering to said mammal an effective amount of a compound of formula (I) or a pharmaceutically acceptable salt thereof:

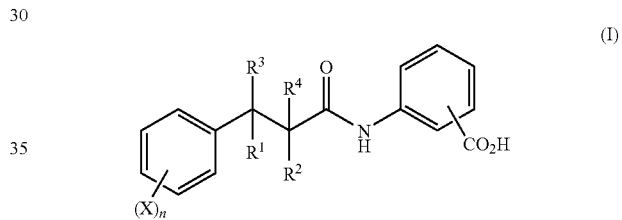

(I)

wherein each of $R^1$ and $R^2$ is independently select d from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to downregulate iNOS expression.

Still another aspect of the present invention provides a method for the treatment and/or prophylaxis of a condition characterised by aberrant, unwanted or otherwise inappropriate microglial cell nitric oxide synthesis in a mammal, said method comprising administering to said mammal an effective amount of a compound of formula (I) or a pharmaceutically acceptable salt thereof:

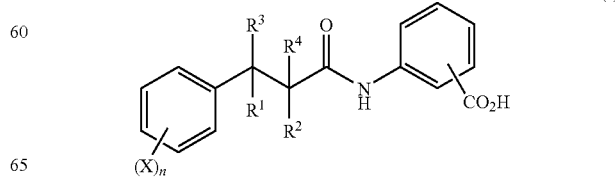

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to downregulate iNOS expression.

Yet another aspect of the present invention provides a method for the treatment and/or prophylaxis of a condition characterised by nitric oxide induced neuronal damage in a mammal, said method comprising administering to said mammal an effective amount of a compound of formula (I) or a pharmaceutically acceptable salt thereof:

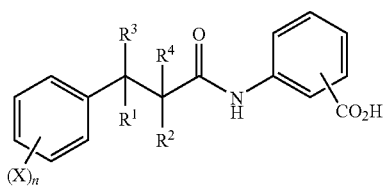

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to downregulate microglial cell iNOS expression.

Preferably, said neuronal damage is brain ischaemia, Parkinson's disease, AIDS dementia, Alzheimer's disease, oligodendrocyte cytotoxicity, demylelination in multiple sclerosis or amyototrophic lateral sclerosis.

Another aspect of the present invention contemplates the use of a compound of formula (I) or a pharmaceutically acceptable salt thereof:

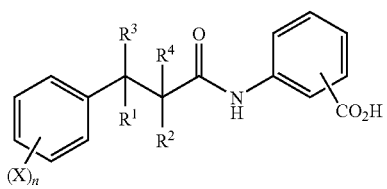

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are allyl or alkoxy groups, they may be connected together to form a ring, and n is an integer from 1 to 3, in the manufacture of medicament for the treatment of a condition in a mammal, which condition is characterised by aberrant, unwanted or otherwise inappropriate microglial cell functional activity, wherein said compounds of formula (I) or pharmaceutically acceptable salts down-regulates microglial cell iNOS expression.

Still yet another aspect of the present invention provides the use of a compound of formula (I) or a pharmaceutically acceptable salt thereof:

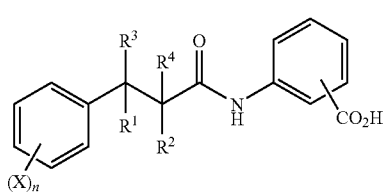

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, in the manufacture of medicament for the treatment of a condition in a mammal, which condition is characterised by aberrant, unwanted or otherwise inappropriate microglial cell nitric oxide synthesis, wherein said compounds of formula (I) or pharmaceutically salts thereof down-regulates microglial cell iNOS expression.

In yet another further aspect, the present invention contemplates a pharmaceutical composition comprising a compound of formula (I) or a pharmaceutically acceptable salt thereof:

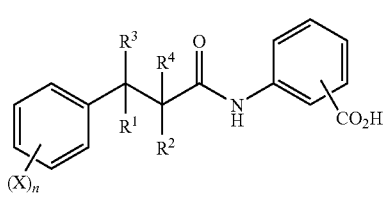

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3 or antagonist thereof as hereinbefore defined and one or more pharmaceutically acceptable carriers and/or diluents.

DETAILED DESCRIPTION OF THE INVENTION

Figure 1:
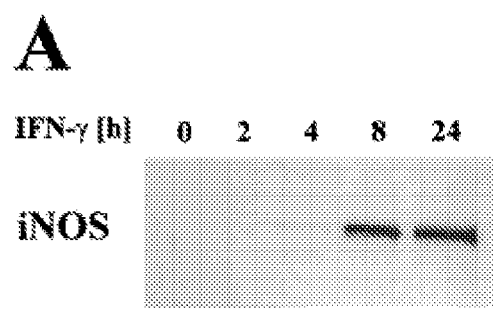
FIG. 1 is an image of 2-[[3-(3,4-dimethoxyphenyl)-1-oxo-2-propenyl]amino]benzoic acid (TNL, tranilast) suppressing iNOS protein expression and activity in N9 microglia in response to IFN-γ. (A) N9 cells were incubated with IFN-γ (200 u ml) and protein lysates were prepared at the time points indicated. Immunoblot analysis was performed using an anti-iNOS antibody revealing a band at ~120 kDa (B) N9 cells were incubated with medium alone, IFN-γ alone (200 u ml) or coincubated with IFN-γ (and 2-[[3-(3,4-dimethoxyphenyl)-1-oxo-2-propenyl]amino]benzoic acid (TNL, 300 μM) or dexamethasone (DEX, 500 nM) for 24 h. (C) N9 cells were stimulated with IFN-γ alone or in combination with dexamethasone (DEX, upper panel) or 2-[[3-(3,4-dimethoxyphenyl)-1-oxo-2-propenyl]amino]benzoic (TNL, lower panel) at the concentrations indicated. Supernatant was collected after 48 h and nitrite was measured using the Griess assay. Values are expressed as $NO_2$ accumulated per $10^5$ cells (mean and s.e. mean, n=3, *P<0.05, P<0.01, *P<0.001).
Figure 1:
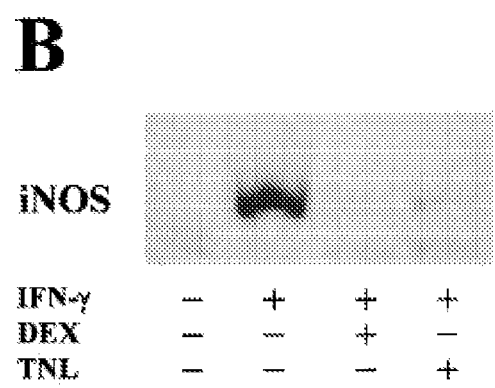
Figure 1:
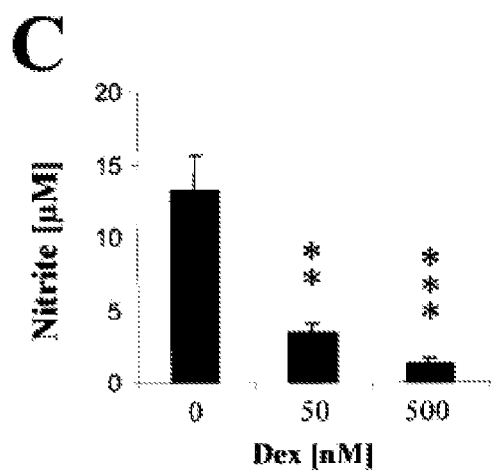
Figure 1:
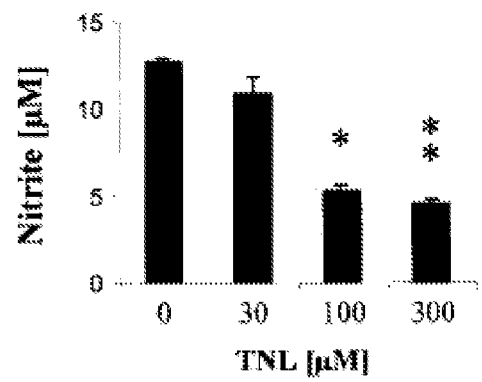

The present invention is predicated, in part, on the surprising determination that compounds of formula (I) inhibit microglial cell functioning and, in particular, microglial iNOS expression. This determination now permits the rational design of therapeutic and/or prophylactic methods for treating conditions characterised by aberrant or otherwise unwanted microglial cell functioning, in particular in terms of iNOS expression. Most particularly, these findings permit the rational design of methods for treating a range of neurological disorders which are characterised by nitric oxide induced neuronal damage—nitric oxide being a downstream by-product of iNOS expression.

Accordingly, one aspect of the present invention provides a method of down-regulating microglial cell functional activity, said method comprising contacting said cell with an effective amount of a compound of formula (I) or a pharmaceutically acceptable salt thereof:

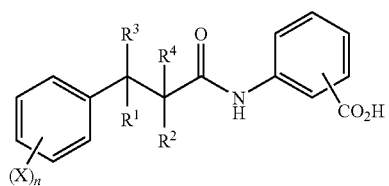

(I)

wherein each of $R^1$ and $R^2$ is independently selected from a hydrogen atom or a $C_1$-$C_4$alkyl group, $R^3$ and $R^4$ are each hydrogen atoms or together form another chemical bond, each X is independently selected from a hydroxyl group, a halogen atom, a $C_1$-$C_4$alkyl group or a $C_1$-$C_4$alkoxy group, or when two X groups are alkyl or alkoxy groups, they may be connected together to form a ring, and n is an integer from 1 to 3, for a time and under conditions sufficient to inhibit, retard or otherwise downregulate iNOS expression.

The carboxyl group may be in the 2-, 3- or 4-position of the aromatic ring. Preferably the carboxyl group is in the 2-position.

Preferably at least one of $R^1$ and $R^2$ is a hydrogen atom. More preferably, both of $R^1$ and $R^2$ are hydrogen atoms.

Preferably $R^3$ and $R^4$ taken together form a chemical bond. Such compounds having an unsaturated bond may be in the form of E or Z geometric isomers.

Preferably n is 1 or 2 and each X, which may be the same or different, is selected from halogen, $C_1$-$C_4$ alkyl or $C_1$-$C_4$alkoxy. Preferably X is selected from halogen and $C_1$-$C_4$alkoxy. More preferably, n is 2 and both X are selected from $C_1$-$C_4$alkoxy, especially when both X are methoxy.

Particularly preferred compounds useful in the invention are those of formula (II):

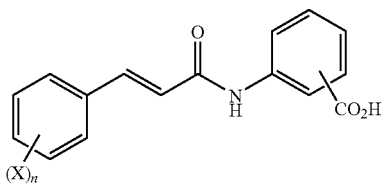

(II)

Examples of compounds of formula (II) include 2-[[3-(2-methylphenyl)-1-oxo-2-propenyl]amino]benzoic acid;
2-[[3-(3-methylphenyl)-1-oxo-2-propenyl]amino]benzoic acid;
2-[[3-(4-methylphenyl)-1-oxo-2-propenyl]amino]benzoic acid;
2-[[3-(2-ethylphenyl)-1-oxo-2-propenyl]amino]benzoic acid;
2-[[3-(3-ethylphenyl)-1-oxo-2-propenyl]amino]benzoic acid;
2-[[3-(4-ethylphenyl)-1-oxo-2-propenyl]amino]benzoic acid;
2-[[3-(2-propylphenyl)-1-oxo-2-propenyl]amino]benzoic acid;
2-[[3-(3-propylphenyl)-1-oxo-2-propenyl]amino]benzoic acid;
2-[[3-(4-propylphenyl)-1-oxo-2-propenyl]amino]benzoic acid;
2-[[3-(2-hydroxyphenyl)-1-oxo-2-propenyl]amino]benzoic acid;
2-[[3-(3-hydroxyphenyl)-1-oxo-2-propenyl]amino]benzoic acid;
2-[[3-(4-hydroxyphenyl)-1-oxo-2-propenyl]amino]benzoic acid;
2-[[3-(2-chlorophenyl)-1-oxo-2-propenyl]amino]benzoic acid;
2-[[3-(3-chlorophenyl)-1-oxo-2-propenyl]amino]benzoic acid;
2-[[3-(4-chlorophenyl)-1-oxo-2-propenyl]amino]benzoic acid;
2-[[3-(2-fluorophenyl)-1-oxo-2-propenyl]amino]benzoic acid;
2-[[3-(3-fluorophenyl)-1-oxo-2-propenyl]amino]benzoic acid;
2-[[3-(4-fluorophenyl)-1-oxo-2-propenyl]amino]benzoic acid;
2-[[3-(2-bromophenyl)-1-oxo-2-propenyl]amino]benzoic acid;
2-[[3-(3-bromophenyl)-1-oxo-2-propenyl]amino]benzoic acid;
2-[[3-(4-bromophenyl)-1-oxo-2-propenyl]amino]benzoic acid;
2-[[3-(2,3-dimethoxyphenyl)-1-oxo-2-propenyl]amino]benzoic acid;
2-[[3-(3,4-dimethoxyphenyl)-1-oxo-2-propenyl]amino]benzoic acid;
2-[[3-(2,4-dimethoxyphenyl)-1-oxo-2-propenyl]amino]benzoic acid;
2-[[3-(2,3-dimethylphenyl)-1-oxo-2-propenyl]amino]benzoic acid;
2-[[3-(3,4-dimethylphenyl)-1-oxo-2-propenyl]amino]benzoic acid;
2-[[3-(2,4-dimethylphenyl)-1-oxo-2-propenyl]amino]benzoic acid;
2-[[3-(2,3-diethoxyphenyl)-1-oxo-2-propenyl]amino]benzoic acid;
2-[[3-(3,4-diethoxyphenyl)-1-oxo-2-propenyl]amino]benzoic acid;
2-[[3-(2,4-diethoxyphenyl)-1-oxo-2-propenyl]amino]benzoic acid;
2-[[3-(2,3-dipropoxyphenyl)-1-oxo-2-propenyl]amino]benzoic acid;
2-[[3-(3,4-dipropoxyphenyl)-1-oxo-2-propenyl]amino]benzoic acid;
2-[[3-(2,4-dipropoxyphenyl)-1-oxo-2-propenyl]amino]benzoic acid;

2-[[3-(2,3-diethylphenyl)-1-oxo-2-propenyl]amino]benzoic acid;
2-[[3-(3,4-diethylphenyl)-1-oxo-2-propenyl]amino]benzoic acid;
2-[[3-(2,4-diethylphenyl)-1-oxo-2-propenyl]amino]benzoic acid;
2-[[3-(2,3-dipropylphenyl)-1-oxo-2-propenyl]amino]benzoic acid;
2-[[3-(3,4-dipropylphenyl)-1-oxo-2-propenyl]amino]benzoic acid;
2-[[3-(2,4-dipropylphenyl)-1-oxo-2-propenyl]amino]benzoic acid;
2-[[3-(2-methoxy-3-methylphenyl)-1-oxo-2-propenyl]amino]benzoic acid,
2-[[3-(3-methoxy-4-methylphenyl)-1-oxo-2-propenyl]amino]benzoic acid;
2-[[3-(2-methoxy-3-methylphenyl)-1-oxo-2-propenyl]amino]benzoic acid;
2-[[3-(2-methoxy-4-methylphenyl)-1-oxo-2-propenyl]amino]benzoic acid;
2-[[3-(2-methoxy-3-chlorophenyl)-1-oxo-2-propenyl]amino]benzoic acid;
2-[[3-(3-methoxy-4-chlorophenyl)-1-oxo-2-propenyl]amino]benzoic acid;
2-[[3-(2-methoxy-3-chlorophenyl)-1-oxo-2-propenyl]amino]benzoic acid;
2-[[3-(2-methoxy-4-chlorophenyl)-1-oxo-2-propenyl]amino]benzoic acid;
2-[[3-(2-methoxy-3-hydroxyphenyl)-1-oxo-2-propenyl]amino]benzoic acid;
2-[[3-(3-methoxy-4-hydroxyphenyl)-1-oxo-2-propenyl]amino]benzoic acid;
2-[[3-(2-methoxy-3-hydroxyphenyl)-1-oxo-2-propenyl]amino]benzoic acid;
2-[[3-(2-methoxy-4-hydroxyphenyl)-1-oxo-2-propenyl]amino]benzoic acid;
2-[[3-(3,4-trimethylenephenyl)-1-oxo-2-propenyl]amino]benzoic acid;
2-[[3-(2,3-trimethylenephenyl)-1-oxo-2-propenyl]amino]benzoic acid;
2-[[3-(3,4-methylenedioxyphenyl)-1-oxo-2-propenyl]amino]benzoic acid; and
2-[[3-(3,4-ethylenedioxyphenyl)-1-oxo-2-propenyl]amino]benzoic acid.

A particularly preferred compound of formula (II) for use in the invention is 2-[[3-(3,4-dimethoxyphenyl)-1-oxo-2-propenyl]amino]benzoic acid.

As used herein, the term "$C_1$-$C_4$alkyl" refers to linear or branched alkyl groups having 1 to 4 carbon atoms. Examples of such groups include methyl, ethyl, n-propyl, isopropyl, n-butyl, sec-butyl and tert-butyl.

As used herein, the term "$C_1$-$C_4$alkoxy" refers to hydroxy groups substituted with linear or branched alkyl groups having 1 to 4 carbon atoms. Examples of such groups include methoxy, ethoxy, n-propoxy, isopropoxy, n-butoxy, sec-butoxy and tert-butoxy.

As used herein, the term "halogen" or "halo" refers to fluoro, chloro or bromo atoms.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

Compounds of formula (I) and their pharmaceutically acceptable salts are known and may be prepared by methods known in the art, see U.S. Pat. No. 3,940,422 the contents of which are incorporated herein by reference.

It will also be recognised that some compounds of formula (I) may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

Without limiting the present invention to any one theory or mode of action, the compounds of formula (I) are orally active anti-allergic compounds which are clinically effective in the control of autoimmune diseases such as bronchial asthma and atopic dermatitis. In this context, it is thought to inhibit the release of various chemical mediators from mast cells. This drug exhibits anti-inflammatory effects and is though to inhibit the synthesis of extracellular matrix of fibroblasts through the suppression of TGFβ. Further, compounds of formula (I) have been shown to prevent restenosis after percutaneous transluminal angioplasty in patients with coronary heart disease. A particularly preferred compound of the invention is known either of the chemical names N-[3,4-dimethoxycinnamoyl]-anthranilic acid or 2-[[3-(3,4-dimethoxyphenyl)-1-oxo-2-propenyl]amino]benzoic acid and may also be referred to as Tranilast. Still further, it is known by the chemical formula $C_{18}H_{17}NO_5$ and by the trade name Rizaben. The structure is depicted below:

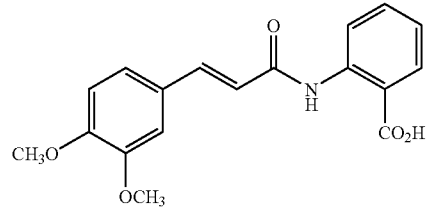

The compounds of formula (I) or pharmaceutically acceptable salts thereof or their antagonists may be linked, bound or otherwise associated with any proteinaceous or non-proteinaceous molecules. For example, in one embodiment of the present invention said compounds of formula (I) or pharmaceutically acceptable salts thereof may be associated with a molecule which permits targeting to a localised region.

Reference to "microglial cell" should be understood as a reference to the small glial cells of mesodermal origin which are distributed throughout the grey and white matter of the brain, although the cells of the present invention should not be limited to those which are found in the brain. The method of the present invention should be understood to extend to microglial cells which occur anywhere in the body. Without limiting the present invention in any way, these cells exhibit scanty cytoplasm and small spine processes. It is thought that these cells are derived from monocytes and invade the neural tissue just before birth. Further, these cells are known to be capable of enlarging to become macrophages. The phrase "microglial cell" should also be understood as a reference to cells which exhibit one or more of the morphology, phenotype and/or functional activity of microglial cells and is also a reference to mutants or variants thereof. "Variants" include, but are not limited to, cells exhibiting some but not all of the morphological or phenotypic features or functional activities of microglial cells at any differentiative stage of development. "Mutants" include, but are not limited to, microglial cells which have been naturally or non-naturally modified such as cells which are genetically modified.

It should also be understood that the microglial cells of the present invention may be at any differentiative stage of development. Accordingly, the cells may be immature and therefore partially functionally incompetent in the absence of further differentiation. In this regard, highly immature cells which retain the capacity to differentiate into microglial cells should nevertheless be understood to satisfy the definition of "microglial cell" as utilised herein due to their capacity to differentiate into microglial cells under appropriate conditions.

Reference to microglial cell "activity" should be understood as a reference to any one or more of the functional activities which an microglial cell is capable of performing, for example, as a result of stimulation by an extracellular agent such as interferon-γ or lipopolysaccharide ("LPS"). Most particularly, said functional activity is one which is directly or indirectly modulated by iNOS expression. In this regard, without limiting the invention to any one theory or mode of action, de novo expression of iNOS is directly linked to the induction of microglial nitric oxide synthesis. In particular, the aberrant overproduction of nitric oxide has been implicated in neurological disorders associated with neuronal damage. Further, microglial derived nitric oxide is thought to play a crucial role in oligodendricyte cytotoxicity and demyelination in multiple sclerosis. Accordingly, in a preferred embodiment the subject microglial cell functional activity is nitric oxide synthesis.

According to this preferred embodiment there is provided a method of down-regulating microglial cell nitric oxide synthesis, said method comprising contacting said cell with an effective amount of a compound of formula (I) or a pharmaceutically acceptable salt thereof for a time and under conditions sufficient to inhibit, retard or otherwise downregulate iNOS expression.

Preferably, said compound of formula (I) is 2-[[3-(3,4-dimethoxyphenyl)-1-oxo-2-propenyl]amino]benzoic acid.

Reference to "iNOS" should be understood as a reference to all forms of this protein and to functional derivatives or homologues thereof. This includes, for example, any isoforms which arise from alternative splicing of the subject iNOS mRNA or mutants or polymorphic variants of these proteins. In this regard, reference to iNOS "expression" should be understood as a reference to the transcription and/or translation of the iNOS gene. Accordingly, downregulation of the "expression" of iNOS should be understood in its broadest sense to encompass downregulation at either of the transcriptional or translational levels.

Without limiting the present invention to any one theory or mode of action, microglial cells upregulate inducible nitric oxide synthase (iNOS) expression in response to pro-inflammatory stimuli such as interferon-γ or lipopolysaccharide. For example, it is though that interferon-γ initiates the synthesis of nitric oxide through the engagement of response elements in the promoter region of the iNOS gene. Induction of iNOS in macrophages by interferon-γ alone is thought to be dependent on the activation of the transcription factor NF-κB. Activation of NF-κB requires phosphorylation of specific serine residues and degradation of IκBα which then dissociates from the NF-κB/IκK complex and allows NF-κB to translocate to the nucleus and bind to κB motifs. Interferon-γ leads to an induction of iNOS mRNA and protein expression accompanied by a release of nitric oxide into the extracellular environment. Accordingly, in a preferred embodiment, said microglial cell functional activity is inflammatory cytokine induced functional activity and, even more preferably, interferon-γ functional activity.

Reference to "inflammatory cytokine induced functional activity" should be understood as a reference to any one or more of the functional activities hereinbefore defined which a microglial cell is capable of performing as a result of inflammatory cytokine stimulation. Cytokines are protein hormones and reference to "cytokine" herein should be understood as a reference to any protein hormone or derivative, homologue, analogue, chemical equivalent or mimetic thereof which induces one or more functional activities which are directly or indirectly associated with an inflammatory response. The subject cytokines include, but are not limited to, interferon-γ. Preferably, the subject cytokine is interferon-γ.

According to this preferred embodiment there is provided a method of down-regulating inflammatory cytokine-induced microglial cell functional activity, said method comprising contacting said cell with an effective amount of a compound of formula (I) or a pharmaceutically acceptable salt thereof for a time and under conditions sufficient to inhibit, retard or otherwise downregulate iNOS expression.

Still more preferably there is provided a method of down-regulating interferon-γ-induced microglial cell functional activity, said method comprising contacting said cell with an effective amount of a compound of formula (I) or a pharmaceutically acceptable salt thereof for a time and under conditions sufficient to inhibit, retard or otherwise downregulate iNOS expression.

Preferably, said compound of formula (I) is 2-[[3-(3,4-dimethoxyphenyl)-1-oxo-2-propenyl]amino]benzoic acid.

Most preferably, said functional activity is nitric oxide synthesis.

In another example, lipopolysaccharide is thought to initiate the synthesis of nitric oxide via an extracellular signal-regulated kinase 2 (ERK-2) related intracellular signalling pathway. Specifically, lipopolysaccharide induces phosphorylation of ERK-2. Tranilast acts by abolishing translocation of protein kinase Cδ (PKCδ) to the nucleus and suppresses the phosphorylation of the PKCδ substrate, myristoylated alaninrich C kinase substrate. Tranilast is thought to affect post-translocation modification of iNOS mRNA. Accordingly, lipopolysaccharide also leads to an induction of iNOS mRNA and protein expression accompanied by a release of nitric oxide into the extracellular environment. Accordingly, in a preferred embodiment, said microglial cell functional activity is lipopolysaccharide induced functional activity.

According to this preferred embodiment there is provided a method of down-regulating lipopolysaccharide-induced microglial cell functional activity, said method comprising contacting said cell with an effective amount of a compound of formula (I) or a pharmaceutically acceptable salt thereof for a time and under conditions sufficient to inhibit, retard or otherwise downregulate iNOS expression.

Preferably, said compound of formula (I) is 2-[[3-(3,4-dimethoxyphenyl)-1-oxo-2-propenyl]amino]benzoic acid.

Most preferably, said functional activity is nitric oxide synthesis.

Without limiting the present invention to any one theory or mode of action, "lipopolysaccharide" describes any of a group of related, 10 kDa, structurally complex components of the outer leaflet of the outer membrane of Gram-negative bacteria lipopolysaccharide molecules consist of three covalently linked regions: lipid A, core oligosaccharide, and an O side chain. The innermost layer, lipid A, which is responsible for the toxicity of the lipopolysaccharide, consists of six fatty acyl chains (sometimes hydroxylated) linked in various ways to two glucosamine residues. The branched core oligosaccharide contains ten saccharide residues, several of them unusual, and has a structure that appears to be similar in closely related bacterial strains. The outermost 0 side chain, which is highly variable and determines the antigenic specificity of the organism, is made up of many (≈50) repeating units of a branched tetrasaccharide containing further unusual sugar residues.

By "interferon-γ" and "lipopolysaccharide" is meant all forms of interferon-γ and lipopolysaccharide, respectively and derivatives, homologues, analogues, chemical equivalents and mimetics thereof. Reference to "interferon-γ" and "lipopolysaccharide" should also be understood to include reference to any isoforms which arise from alternative splicing of interferon-γ and lipopolysaccharide mRNA or mutants or polymorphic variants of interferon-γ and lipopolysaccharide. It should also be understood to include reference to any other molecule which exhibits interferon-γ or lipopolysaccharide functional activity to the extent that the subject molecule mimics one or more interferon-γ or lipopolysaccharide signalling events by inducing signalling through a interferon-γ or lipopolysaccharide or interferon-γ-like or lipopolysaccharide-like receptor. Since the method of the present invention is directed to modulating a cellular activity by modulating an intracellular event which has been induced as a result of the interaction of interferon-γ or lipopolysaccharide with its receptor, this methodology can be applied to modulating such a cellular activity, irrespective of whether it has been induced by the interaction of interferon-γ or lipopolysaccharide with an interferon-γ receptor or lipopolysaccharide receptor or the interaction of a interferon-γ or lipopolysaccharide mimetic, such as a naturally occurring or non-naturally occurring mimetic or analogue, with the subject receptor. It is conceivable, for example, that there may be naturally or non-naturally occurring interferon-γ or lipopolysaccharide mimetics (for example, toxins or drugs) which, if they were introduced into an individual, would induce unwanted interferon-γ-like or lipopolysaccharide-like cellular activities due to their interaction with the interferon-γ receptor or lipopolysaccharide receptor. Accordingly, the present invention should be understood to extend to the modulation of such cellular activities which are herein defined as falling within the scope of being "interferon-γ-induced" or "lipopolysaccharide induced".

"Derivatives" of the proteins herein described include fragments, parts, portions, mutants, variants and mimetics from natural, synthetic or recombinant sources including fusion proteins. Parts or fragments include, for example, active regions of interferon-γ. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

Reference to "homologues" should be understood as a reference to molecules derived from species other than the species being treated.

Chemical and functional equivalents of a protein molecule should be understood as molecules exhibiting any one or more of the functional activities of these molecules and may be derived from any source such as being chemically synthesized or identified via screening processes such as natural product screening.

The derivatives include fragments having particular epitopes or parts of the entire protein fused to peptides, polypeptides or other proteinaceous or non-proteinaceous molecules.

Analogues contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl--aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |

TABLE 1-continued

| Non-conventional amino acid | Code | Non-conventional amino acid | Code |
|---|---|---|---|
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanin | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl- ethylamino)cyclopropane | Nmbc | | |

Crosslinkers can be used, for example, to stabilise 3D conformations, using homo-bifuncfional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

Reference to the tranilast molecule should be understood to encompass reference to chemical and functional equivalents of tranilast exhibiting any one or more of the functional activities of tranilast, which functional equivalents may be derived from any source such as being chemically synthesised or identified via screening processes such as natural product screening. For example chemical or functional equivalents of tranilast can be designed and/or identified utilising well known methods such as combinatorial chemistry or high throughput screening of recombinant libraries or following natural product screening.

For example, libraries containing small organic molecules may be screened, wherein organic molecules having a large number of specific parent group substitutions are used. A general synthetic scheme may follow published methods (eg., Bunin et al., 1994; DeWitt et al., 1993). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. In the present context, for example, they may be used as a starting point for developing tranilast analogues which exhibit properties such as more potent pharmacological effects. Tranilast or a functional part thereof may according to the present invention be used in combination libraries formed by various solid-phase or solution-phase synthetic methods (see for example U.S. Pat. No. 5,763,263 and references cited therein). By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analysed.

With respect to high throughput library screening methods, oligomeric or small-molecule library compounds capable of interacting specifically with a selected biological agent, such as a biomolecule, a macromolecule complex, or cell, are screened utilising a combinational library device which is easily chosen by the person of skill in the art from the range of well-known methods, such as those described above. In such a method, each member of the library is screened for its ability to interact specifically with the selected agent. In practising the method, a biological agent is drawn into compound-containing tubes and allowed to interact with the individual library compound in each tube. The interaction is designed to produce a detectable signal that can be used to monitor the presence of the desired interaction. Preferably, the biological agent is present in an aqueous solution and further conditions are adapted depending on the desired interaction. Detection may be performed for example by any well-known functional or non-functional based method for the detection of substances.

In addition to screening for molecules which mimic the activity of tranilast, it may also be desirable to identify and utilise molecules which function agonistically or antagonistically to tranilast in order to up or downregulate the functional activity of tranilast in relation to modulating microglial cell functioning. The use of such molecules is described in more detail below. To the extent that the subject molecule is proteinaceous, it may be derived, for example, from natural or recombinant sources including fusion proteins or following, for example, the screening methods described above. The non-proteinaceous molecule may be, for example, a chemical or synthetic molecule which has also been identified or generated in accordance with the methodology identified above. Accordingly, the present invention contemplates the use of chemical analogues of tranilast capable of acting as agonists or antagonists. Chemical agonists may not necessarily be derived from tranilast but may share certain conformational similarities. Alternatively, chemical agonists may be specifically designed to mimic certain physiochemical properties of tranilast. Antagonists may be any compound capable of blocking, inhibiting or otherwise preventing tranilast from carrying out its normal biological functions. Antagonists include monoclonal antibodies specific for tranilast or parts of tranilast.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 1.

As detailed above, the present invention is predicated on the determination that compounds of formula (I) and pharmaceutically acceptable salts thereof function to down-regulate microglial cell functional activity. Without limiting the present invention to any one theory or mode of action, it is thought that the downregulation of microglial cell functional activity involves direct inhibition of microglial cell functional activity by suppression of the iNOS expression. It should be understood, however, that the compounds of formula (I) or pharmaceutically acceptable salts thereof may also act on microglial cells via indirect mechanisms. Reference to "downregulating" microglial cell functional activity should therefore be understood as a reference to preventing, reducing (eg. slowing) or otherwise inhibiting one or more aspects of the functional activity of the cell while reference to "up-regulating" (to the extent that it is discussed hereinafter) should be understood to have the converse meaning.

It should be understood that the cell which is treated according to the method of the present invention may be located ex vivo or in vivo. By "ex vivo" is meant that the cell has been removed from the body of a subject wherein the modulation of its activity will be initiated in vitro. For example, the cell may be a microglial cell which is to be used as a model for studying any one or more aspects of the pathogenesis of neurological conditions which are characterised by aberrant microglial cell nitric oxide synthesis. In a preferred embodiment, the subject cell is located in vivo.

According to this preferred embodiment there is provided a method of down-regulating microglial cell functional activity in a mammal, said method comprising administering to said mammal an effective amount of a compound of formula (I) or a pharmaceutically acceptable salt thereof for a time and under conditions sufficient to inhibit, retard or otherwise downregulate iNOS expression.

Preferably, said compound of formula (I) is 2-[[3-(3,4-dimethoxyphenyl)-1-oxo-2-propenyl]amino]benzoic acid.

More preferably, said functional activity is nitric oxide synthesis.

In a most preferred embodiment there is provided a method of down-regulating inflammatory cytokine-induced microglial cell nitric oxide synthesis in a mammal, said method comprising administering to said mammal an effective amount of a compound of formula (I) or a pharmaceutically acceptable salt thereof for a time and under conditions sufficient to inhibit, retard or otherwise downregulate iNOS expression.

Still more preferably there is provided a method of down-regulating interferon-γ-induced microglial cell nitric oxide synthesis in a mammal, said method comprising administering to said mammal an effective amount of a compound of formula (I) or a pharmaceutically acceptable salt thereof for a time and under conditions sufficient to inhibit, retard or otherwise downregulate iNOS expression.

In another preferred embodiment, there is provided a method of down-regulating lipopolysaccharide-induced microglial cell nitric oxide synthesis in a mammal, said method comprising administering to said mammal an effective amount of a compound of formula (I) or a pharmaceutically acceptable salt thereof for a time and under conditions sufficient to inhibit, retard or otherwise downregulate iNOS expression.

Preferably, said compound of formula (I) is 2-[[3-(3,4-dimethoxyphenyl)-1-oxo-2-propenyl]amino]benzoic acid.

The term "mammal" as used herein includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Preferably, the mammal is human or a laboratory test animal Even more preferably, the mammal is a human. Although the present invention is exemplified herein with respect to laboratory test animals, this should not be understood in any way as limiting the application of the present invention to humans.

Although the preferred method is to downregulate the functional activity of microglial cells in order to minimise unwanted nitric oxide synthesis, it may also be desired to induce the up-regulation of tranilast inhibited microglial cell functioning. For example, in certain non-neurological conditions (such as allergies or autoimmune diseases such as bronchial asthma or atopic dermatitis), the administration of tranilast is a known therapy. Accordingly, a side effect of such therapy may well lead to inhibition of microglial cell functioning, in particular nitric oxide synthesis. Although this may often correlate to a positive side-effect, due to the generally unwanted nature of nitric oxide secretion, in certain circumstances there may occur physiological situations in which a certain level of microglial nitric oxide synthesis is desirable. Accordingly, to the extent that it is not possible to rectify this situation by ceasing administration of compounds of formula (I), it may be desirable to administer, (in a site directed manner, for example) an antagonistic agent of compounds of formula (I). In another example, therapy with compounds of formula (I) may necessitate the use of antagonists of compounds of formula (I) in order to inhibit the functioning of the compounds which has been introduced to a mammal but which functional activity is required to be slowed or stopped. Reference to "compound of formula (I) inhibited microglial cell functioning" should therefore be understood to mean that at least some of the microglial cell population of the mammal exhibit inhibited, slowed or otherwise retarded functioning due to the functional effects of the compound of formula (I) or a pharmaceutically acceptable salt thereof.

Accordingly, another aspect of the present invention is directed to a method of upregulating microglial cell inhibited functional activity in a mammal, said method comprising administering to said mammal an effective amount of an antagonist of a compound of formula (I) or a pharmaceutically acceptable salt thereof for a time and under conditions sufficient to upregulate iNOS expression.

Reference to "antagonist of a compound of formula (I) or a pharmaceutically acceptable salt thereof" should be understood as a reference to any proteinaceous or non-proteinaceous molecule which directly or indirectly inhibits, retards or otherwise downregulates the cell functioning inhibitory activity of the compounds of formula (I) or pharmaceutically salts thereof. Identification of antagonists suitable for use in the present invention can be routinely achieved utilising methods well known to those skilled in the art.

A further aspect of the present invention relates to the use of the invention in relation to the treatment and/or prophylaxis of disease conditions. Without limiting the present invention to any one theory or mode of action, the pleiotropic activity of cytokines, and in particular interferon-γ, renders these molecules an integral functional component of every aspect of both healthy and disease state physiological processes. Accordingly, the method of the present invention provides a valuable tool for modulating aberrant or otherwise unwanted interferon-γ-induced microglial cell functional activity. It should be understood, however, that the present invention extends to the treatment and/or prophylaxis of disease conditions characterised by aberrant or otherwise unwanted microglial cell activity, per se, irrespective of the stimulatory signal, and in particular aberrant nitric oxide synthesis.

Accordingly, in another aspect the present invention contemplates a method for the treatment and/or prophylaxis of a condition characterised by aberrant, unwanted or otherwise inappropriate microglial cell functional activity in a mammal, said method comprising administering to said mammal an effective amount of a compound of formula (I) or a pharmaceutically acceptable salt thereof for a time and under conditions sufficient to downregulate iNOS expression.

Reference to "aberrant, unwanted or otherwise inappropriate" microglial cell functioning should be understood as a reference to overactive cell functioning or to physiologically normal cell functioning which is inappropriate in that it is unwanted. For example, overproduction of nitric oxide has been implicated in neurological disorders associated with neuronal damage including brain ischaemia, Parkinson's disease, AIDS dementia, Alzheimer's disease, oligodendrocyte cytotoxicity, demylelination in multiple sclerosis and amyototrophic lateral sclerosis.

In a preferred embodiment, the present invention contemplates a method for the treatment and/or prophylaxis of a condition characterised by aberrant, unwanted or otherwise inappropriate microglial cell nitric oxide synthesis in a mammal, said method comprising administering to said mammal an effective amount of a compound of formula (I) or a pharmaceutically acceptable salt thereof for a time and under conditions sufficient to downregulate iNOS expression.

More preferably, the present invention contemplates a method for the treatment and/or prophylaxis of a condition characterised by nitric oxide induced neuronal damage in a mammal, said method comprising administering to said mammal an effective amount of a compound of formula (I) or a pharmaceutically acceptable salt thereof for a time and under conditions sufficient to downregulate microglial cell iNOS expression.

Most preferably, said neuronal damage is brain ischaemia, Parkinson's disease, AIDS dementia, Alzheimer's disease, oligodendrocyte cytotoxicity, demylelination in multiple sclerosis or amyototrophic lateral sclerosis.

More preferably, said compound of formula (I) is 2-[[3-(3,4-dimethoxyphenyl)-1-oxo-2-propenyl]amino]benzoic acid.

In accordance with these preferred embodiments, said aberrant microglial cell functional activity is preferably inflammatory cytokine induced microglial cell activity, in particular interferon-γ induced microglial cell activity, or lipopolysaccharide induced microglial cell activity.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The present invention further contemplates a combination of therapies, such as the administration of compounds of formula (I) or pharmaceutically salts thereof together with subjection of the mammal to other agents which are useful in the treatment of neurological degeneration.

Administration of the compounds of formula (I) or pharmaceutically salts thereof or antagonist thereof (herein referred to as "modulatory agent"), in the form of a pharmaceutical composition, may be performed by any convenient means. The modulatory agent of the pharmaceutical composition is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 mg to about 1 mg of modulatory agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The modulatory agent may be administered in a convenient manner such as by the oral, intravenous (where water soluble), intraperitoneal, intramuscular, subcutaneous, intradermal or suppository routes or implanting (e.g. using slow release molecules). The modulatory agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip patch and implant.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. For example, the subject agent may be administered together with an agonistic agent in order to enhance its effects. By "sequential" administration is meant a time difference of from seconds, minutes, hours or days between the administration of the two types of molecules. These molecules may be administered in any order.

Another aspect of the present invention contemplates the use of a compound of formula (I) or pharmaceutically acceptable salts thereof, in the manufacture of medicament for the treatment of a condition in a mammal, which condition is characterised by aberrant, unwanted or otherwise inappropriate microglial cell functional activity, wherein said compound of formula (I) or a pharmaceutically acceptable salt thereof down-regulates microglial cell iNOS expression.

More preferably, the present invention contemplates the use of a compound of formula (I) or pharmaceutically acceptable salts thereof, in the manufacture of medicament for the treatment of a condition in a mammal, which condition is characterised by aberrant, unwanted or otherwise inappropriate microglial cell nitric oxide synthesis, wherein said compound of formula (I) or a pharmaceutically acceptable salt thereof down-regulates microglial cell iNOS expression.

More preferably, said compound of formula (I) 2-[[3-(3,4-dimethoxyphenyl)-1-oxo-2-propenyl]amino]benzoic acid.

Most preferably, said neuronal damage is brain ischaemia, Parkinson's disease, AIDS dementia, Alzheimer's disease, oligodendrocyte cytotoxicity, demyelination in multiple sclerosis or amyotrophic lateral sclerosis.

In accordance with these preferred embodiments, said aberrant microglial cell functional activity is preferably inflammatory cytokine induced microglial cell activity, in particular interferon-γ induced microglial cell activity, or lipopolysaccharide-induced microglial cell activity.

In yet another further aspect, the present invention contemplates a pharmaceutical composition comprising a compound of formula (I) or a pharmaceutically acceptable salts thereof or antagonist thereof as hereinbefore defined and one or more pharmaceutically acceptable carriers and/or diluents. Said agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Yet another aspect of the present invention relates to compounds of formula (I) or pharmaceutically acceptable salts thereof or antagonists thereof, as hereinbefore defined, when used in the method of the present invention.

The present invention is further defined by the following non-limiting examples:

EXAMPLE 1

2-[[3-(3,4-Dimethoxyphenyl)-1-oxo-2-propenyl]amino]benzoic Acid (Tranilast) Suppresses Microglial Inducible Nitric Oxide Synthase (iNOS) Expression and Activity Induced by Interferon-γ (IFN-γ)

Materials and Methods

Reagents and Cell Culture

Tranilast was a generous gift of Kissei Pharmaceuticals (Nagano, Japan). Murine recombinant IFN-γ was purchased from Boehringer (Mannheim, Germany). Dexamethasone (DEX) was obtained from Sigma (Deisenhofen, Germany). N9 murine microglial cells were a kind gift from P. Ricciardi-Castagnoli (Milano, Italy) (Righi, M., Mori, L., De Libero, G., Sironi, M., Biondi, A., Mantovani, A., Donini, S. D. and Ricciardi-Castagnoli, P. *Eur J Immunol* 19(8):1443-1448, 1989). The cells were cultured in Dulbecco's modified Eagle's medium (DMEM) supplemented with 10% foetal calf serum (FCS), 2 mM glutamine and penicillin (100 μml)/streptomycin (100 μg ml), and maintained at 37° C. in an atmosphere of 5% $CO_2$. Viability was assessed by crystal violet staining.

iNOS Activity iNOS activity was assessed by the Griess assay as described elsewhere (Rieger, J., Stander, M., Loschmann, P. A., Heneka, M., Dichgans, J., Klockgether, T. and Weller, M., *Oncogene*, 17:2323-2332, 1998). Briefly, conditioned supernatant (100 μl) was incubated with an equal volume of 1% sulphanilamide/0.1% naphthyl ethylene diamine dihydrochloride/2.5% $H_3PO_4$ (Griess reagent) (Green, L. C., Wagner, D. A., Glogowski, J., Skipper, P. I., Wishnok, J. S, and Tannenbaum, S. R., *Anal. Biochem.*, 126:131-138, 1982), incubated for 5 min at room temperature, and the absorbance at 546 n=was determined. Solutions of $NaNO_2$ diluted in DMEM served as standards. The absorbance readings resulting from DMEM alone were subtracted from the sample values. Cell density was assessed using crystal violet staining to control for differences in cell proliferation. iNOS activity is thus expressed here as $NO_2$ accumulated per 48 h per $10^5$ cells.

Immunoblot Analysis

For the preparation of whole cell lysates, the cells were rinsed in phosphate-buffered saline (PBS), harvested, centrifuged at 1200×g, lysed in 0.1 M TRIS-HCl (pH 7.2) containing 0.1% NP40, 0.1 mM EDTA and 5 μg ml PMSF for 40 min on ice, and centrifuged at 10,000×g for 10 min. Protein concentration was determined using Biorad reagents with photometric analysis. Proteins (20 μg lane) were separated by 10-12% SDS-PAGE and electroblotted on nitrocellulose. qual protein loading was controlled by Ponceau S staining. After blocking for 1 h in PBS supplemented with 5% skimmed milk and 0.1% Tween 20, immunodetection was performed using ani-iNOS rabbit polyclonal antibody (1:1000, Cayman, Ann Arbor, Mich., USA) and antiphospho-IκBα mouse monoclonal antibody (1:1000, New England Biolabs, Frankfurt am Main, Germany). Bands were visualized using horseradish peroxidase (HRP)-conjugated anti-rabbit IgG (1:4000, Santa Cruz Biotechnology) or anti-mouse IgG (1:4000, Amersham) and enhanced chemoluminescence (ECL) (Amersham).

Northern Blot Analysis

Total RNA was isolated using the RNeasy kit (Qiagen, Hilden, Germany). Total RNA (10 g) was separated on 1.2% agarose gels and blotted onto nylon membranes (Amersham). The filters were hybridized according to standard procedures (Platten, M., Wild-Bode, C., Wick, W., Leitlein, J., Dichgans, J., and Weller, M., *Int. J. Cancer*, 93:53-61, 2001) with a $^{32}$P-labelled murine cDNA probe for iNOS. For the generation of the iNOS probe, N9 cells were stimulated with IFN-γ (2001 ml) for 24 h. Total RNA (5 μg) was subjected to reverse transcription using SuperScript II (Gibco-BRL, Gaithersburg, Md., USA) and oligo-dT priming (Amersham Pharmacia Biotech, Uppsala, Sweden). iNOS fragments were PCR-amplified using primers 5'-AAGCTGCATGTGACATCGAC-3' (SEQ ID NO: 1) and 5'-ATGTGTCTGCAGATGTGCTG-3' (SEQ ID NO: 2) corresponding to nucleotides 386-405 and 839-858 of murine iNOS cDNA. Equal loading was assured by ethidium bromide staining.

NF-κB Reporter Assay

N9 murine microglial cells were seeded in a 96-well plate ($8×10^3$ well) and allowed to adhere for 24 h. The cells were transfected with an NK-κB cis-reporter gene plasmid (Path-Detect* no. 219077, Stratagene) which encodes firefly luciferase in a NF-κB-dependent-manner. For each transfection, 0.2 μg DNA and 0.6 μl FuGene (Roche, Mannheim, Germany) were used. The cells were either co-transfected with 0.02 μg of the pFC-Mekk positive control plasmid, included in the NF-κB cis-reporting system from Stratagene, or with the pcDNA-3 plasmid, to maintain a constant amount of total DNA. In order to assess the unspecific background, a control transfection with pcDNA-3 only was included in all experiments. After 24 h the cells were washed twice with PBS (0.12 M NaCl, 0.01 M $NaH_2PO_4×H_2O$, 0.031 M $K_2HPO_4$) and lysed using 40 μl well of Cell Lysis Buffer (mM):tricine pH 7.8 40, NaCl 50, EDTA 2, $MgSO_4$ 1, DTT 5, 1% Triton* X-100, all from Sigma. To optimize lysis, a freeze-thaw cycle was performed. Then the lysate was transferred to a LumiNunc™ plate (Nunc, Roskilde, Denmark). Luciferase assay reagent (100 μl) containing (mM): tricine pH 7.8 40, $MgSO_4$ 10, EDTA 0.5, DTT 10, coenzyme A 0.5 and beetle luciferin 0.5, (0.5 M ATP), (all from Sigma) were added and luminescence was measured in a LumimatPlus (EG&G Berthold, Pforzheim, Germany). Background was subtracted from all values and the remaining luciferase activity was expressed in percent of the positive control (pFC-Mekk transfection). Thus, the results become independent from transfection efficiency. The value of the positive control remained largely unchanged through all treatment groups.

Statistical Analyses

Experiments were usually performed in triplicate and repeated three times. The significance was evaluated by t-test or ANOVA at $P<0.05$, $P<0.01$ or $P<0.001$.

Results

Tranilast Suppresses Microglial iNOS Protein Expression and Activity Induced by IFN-γ

While N9 microglial cells displayed no constitutive iNOS protein expression, incubation with IFN-γ (200 u ml) induced strong iNOS protein expression in N9 cells in a time-dependent manner as measured by immunoblot analysis. iNOS protein was weakly detectable 4 h after stimulation, strongly induced after 8 h and lasted for at least 24 h (FIG. 1A). Addition of tranilast (300 µM) greatly suppressed IFN-γ-induced iNOS protein expression as did dexamethasone (500 nM) (FIG. 1B). No detectable amounts of $NO_2$ were measured in the conditioned medium of untreated N9 cells indicating that there was no constitutive iNOS activity (data not shown). When stimulated with IFN-γ (200 u ml) the cells released 13 µM (±3 µM) $NO_2$ per 48 h per $10^5$ cells. Addition of tranilast led to a concentration-dependent inhibition of NO release with a reduction by 65% at 300 µM. In comparison, addition of 500 nM dexamethasone reduced the amount of $NO_2$ by 75% (FIG. 1C).

Tranilast Suppresses Microglial iNOS mRNA Expression Induced by IFN-γ

Figure 2:
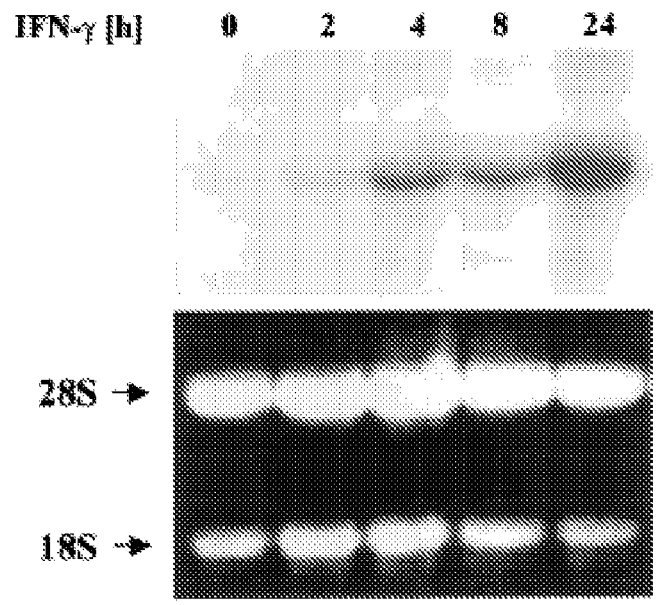
FIG. 2 is an image of 2-[[3-(3,4-dimethoxyphenyl)-1-oxo-2-propenyl]amino]benzoic acid (TNL, tranilast) suppressing iNOS mRNA expression in N9 microglia in response to IFN-γ. (A) N9 cells were incubated with IFN-γ (200 u ml) and mRNA was prepared at the time points indicated. Northern blot analysis was performed using an iNOS cDNA probe revealing a band running at ~1.2 kB. Equal loading was assured by ethidium bromide staining of the 18 S and 28 S ribosomal fractions. (B) N9 cells were incubated with 2-[[3-(3,4-dimethoxyphenyl)-1-oxo-2-propenyl]amino]benzoic acid (30-300 µM) and stimulated with IFN-γ (200 u ml) for 24 h. Northern blot analysis was performed as in (A).
Figure 2:
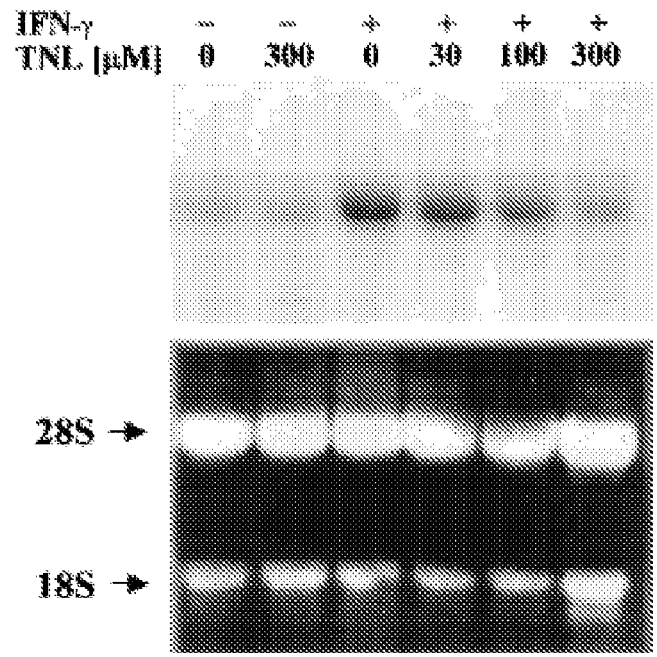

IFN-γ (200 u ml) induced strong iNOS mRNA expression in N9 cells in a time-dependent manner as assessed by Northern Blot (FIG. 2A). Coincubation with tranilast (300 µM) greatly suppressed iNOS mRNA expression, indicating that tranilast inhibits iNOS induction on a transcriptional level (FIG. 2B).

Tranilast Suppresses NF-κB Activation Induced by IFN-γ in N9 Microglia

Figure 3:
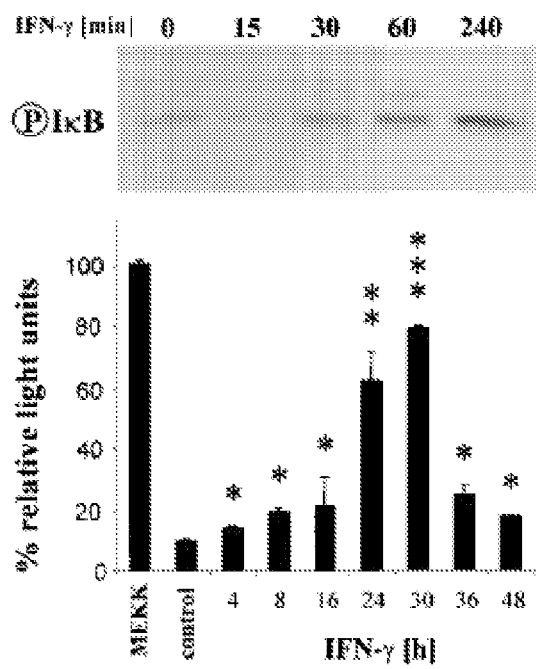
FIG. 3 is an image of 2-[[3-(3,4-dimethoxyphenyl)-1-oxo-2-propenyl]amino]benzoic acid (TNL, tranilast) suppressing NF-κB activation and IκBα phosphorylation in N9 microglia in response to IFN-γ. N9 cells were incubated with IFN-γ (200 u ml) with or without a 4 h preincubation with 2-[[3-(3,4-dimethoxyphenyl)-1-oxo-2-propenyl]amino]benzoic (30-300 µM) and protein lysates were prepared at the time points indicated. Immunoblot analysis was performed using an anti-phospho-IκBα antibody (A, B, upper panels). In parallel, N9 cells were transiently transfected with an NF-κB reporter plasmid or MEKK plasmid serving as a positive control. After 24 h cells were incubated with IFN-γ (200 u ml) with or without a 4 h preincubation with 2-[[3-(3,4-dimethoxyphenyl)-1-oxo-2-propenyl]amino]benzoic acid (30-300 µM). Luciferase activity was determined as described. Values are expressed as percent relative light units of the positive control. Data are expressed as mean and s.e. mean (n=3, *P<0.05, P<0.01, *P<0.001, effect of IFN-γ compared to control (A); *P<0.05, **P<0.01, effect of IFN-γ+TNL compared with IFN-γ alone (B)) (A, B, lower panel).
Figure 3:
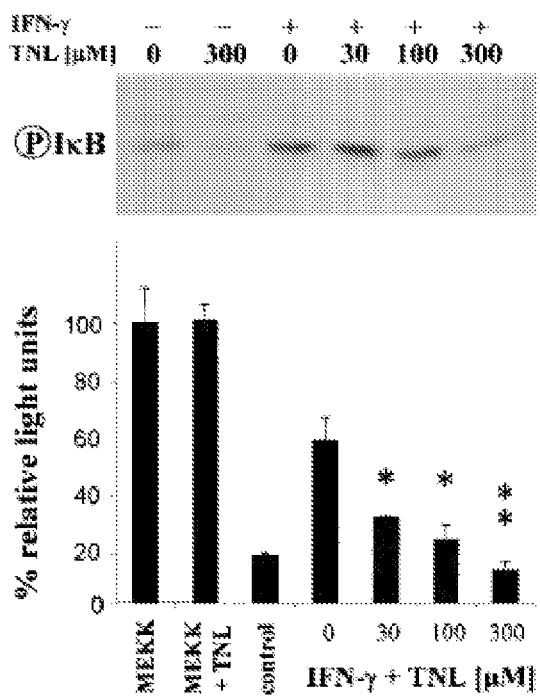

Since NF-κB is an essential transcription factor for the induction of iNOS gene expression, we next asked whether tranilast modulates the activation of NF-κB in response to IFN-γ. At 24 h after transfection with an NF-κB reporter gene plasmid, incubation with IFN-γ (200 u ml) led to a time-dependent activation of luciferase activity. Of note, there was a small but significant increase of luciferase activity 4 h after stimulation with IFN-γ which peaked after 30 h. There was an induction of protein expression of phosphorylated IκB by IFN-γ preceding the activation of NF-κB reporter gene activity as measured by immunoblot analysis (FIG. 3A). When coincubated with tranilast, there was a concentration-dependent suppression of IκB phosphorylation and NF-κB reporter gene activity (FIG. 3B).

EXAMPLE 2

Involvement of Protein Kinase Cδ and Extracellular Signal-Related Kinase-2 in the Suppression of Microglial Inducible Nitric Oxide Synthase Expression by N-[3,4-Dimethoxycinnamoyl]-Anthranilic Acid (Tranilast)

Methods

Reagents and Cell Culture

TNL was a generous gift of Kissei Pharmaceuticals, LPC (*Escherichia coli*, 0127:BS), phorbol 12-myristate 13-acetate (PMA) and dexamethasone (DEX) were obtained from Sigma, BAY 11-7082 (BAY), NF-κB SN50 inhibitory peptide (SN50), GF 109203X (GFX) and rottlerin (ROT) were purchased from Biomol. PD098059 (PD) was obtained from Calbiochem. Purified murine interferon-γ (IFN-γ) was purchased from Roche Diagnostics. N9 murine microglial cells were a kind gift from P. Ricciardi-Castagnoli (Righi, M. et al. 1989 supra). Cells were cultured in Dulbecco's modified Eagle's medium (DMEM) supplemented with 10% fetal calf serum (FCS), 2 mM glutamine, penicillin (100 unit/mL) and streptomycin (100 µg/mL) and maintained at 37° in an atmosphere of 5% $CO_2$. Viability was assessed by crystal violet staining.

iNOS Activity iNOS activity was assessed by the Griess assay (Platten, M., Wick, W., Wischhusen, J. and Weller, M. *Br J Pharmacol* 134(6):1279-1284, 2001). Briefly, conditioned supernatant was incubated with an equal volume of Griess reagent containing 1% sulphanilamide, 0.1% naphthylethylenediamine dihydrochloride and 2.5% $H_3PO_4$ (Green, L. C., Wagner, D. A., Glogowski, J., Skipper, P. I., Wishnok, J. S, and Tannenbaum, S. R. *Anal. Biochem.*, 126:131-138, 1982) for 5 min. at room temperature. The absorbance was measured at 546 nm. $NaNO_2$ diluted in DMEM served as a standard. To control for cell number, the cells were stained with crystal violet. iNOS activity is expressed as nitrite accumulated in 48 hr/$10^5$ cells.

Immunoblot Analysis

For the preparation of whole cell lysates, the cells were lysed in 0.1 M Tris-HCl (pH 7.2) containing 0.1% NP40, 0.1 mM EDTA and 5 µg/mL phenylmethylsulphonyl fluoride. Twenty micrograms protein was separated by 10-12% SDS-PAGE and electroblotted on nitrocellulose membrane. Equal loading was controlled by Ponceau S staining. Immunodetection was performed using the following antibodies: anti-iNOS rabbit polyclonal antibody (1:1000, Cayman), antiphospho-IκBα mouse monoclonal antibody (1:1000), anti-PKCδ mouse monoclonal antibody (1:2000), antiphospho-MARCKS rabbit polyclonal antibody (1:1000), antiphospho-ERK-1/2, antiphospho-AKT, antiphospho-p38 mouse monoclonal antibodies (1:2000), anti-ERK-1/2, anti-AKT mouse monoclonal antibodies (1:500, all from Signal Transduction Laboratories). Bands were visualized using horseradish peroxidase-conjugated anti-rabbit IgG (1:4000 SantaCruz) or anti-mouse IgG (1:4000, Amersham).

Northern Blot Analysis

RNA was isolated using the RNeasy™ kit (Qiagen). Total RNA (10 µg) was separated on 1.2% agarose gels and blotted onto nylon membranes (Amersham). The filters were hybridized according to standard procedures with a $^{32}$P-labeled murine cDNA probe for iNOS. For the generation of the iNOS probe, N9 cells were stimulated with IFN-γ (200 unit/mL) for 24 hr. Total RNA was subjected to reverse transcription using SuperScript II (Gibco-BRL) and oligo-dT priming (Amersham Pharmacia Biotech). iNOS fragments were PCR-amplified using primers 5'AAGCTGCATGTGACATCGAC-3' and 5-ATGTGTCTGCAGATGTGCTG-3' corresponding to nucleotides 386-405 and 839-858 of murine iNOS cDNA. Equal loading was controlled by ethidium bromide staining.

NF-κB Reporter Assay

NF-κB reporter gene activity was assayed as previously described (Platten, M. et al. 2001 supra). Briefly, 8×$10^3$ cells/well were seeded in a 96-well plate and transfected with an NF-κB cis reporter gene plasmid (PathDetect No. 219077, Stratagene) encoding firefly luciferase using FuGene™ transfection reagent (Roche). pFC-MEKK (Stratagene) and pcDNA3 plasmids cotransfected with the reporter plasmid served as positive and negative controls. After freezing and thawing, the cells were lysed in 40 mM Tricine (pH 7.8) containing 50 mM NaCl, 2 mM EDTA, 1 mM $MgSO_4$, 5 mM DTT and 1% Triton X-100. Lysates were assayed using Luciferase assay reagent (40 mM Tricine, pH 7.8, containing 10 mM $MgSO_4$, 0.5 mM EDTA, 10 mM DTT, 0.5 mM coenzyme A, 0.5 M ATP and 0.5 mM beetle luciferine). Luminescence was measured in LumiNunc™ plates (Nunc) in a LumimatPlus™ (EG&G Berthold). Values are expressed as relative light units (RLU).

Immunocytochemistry

Cells grown on glass coverslips were serum-starved for 16 hr, kept in Krebs Ringer HEPES buffer (125 mM NaCl, 5 mM KCl, 1.2 mM $MgSO_4$, 2 mM $CaCl_2$, 1.2 mM $KH_2PO_4$, 6 mM glucose, 25 mM HEPES, pH 7.4) for 1 hr and left untreated or treated with PMA (100 nM) without or with pre-incubation (1 hr) with TNL (300 µM). After fixation in ice-cold (–20') methanol for 20 min, the cells were washed with PBS and incubated for 15 min with 0.1% $NaBH_4$ and 0.1 M glycine in PBS to block autofluorescence. Nonspecific antibody binding was blocked for 45 min with PBG (PBS with 0.045% fish gelatin) containing 5% normal goat serum and 1% bovine serum albumin. Incubation with anti-PKCδ antibody was carried out for 24 hr at 4° after dilution in PBG containing 5% normal goat serum. After four washes with PBG, primary antibody binding was detected with an isotype-specific secondary antibody conjugated with Alexa™546 fluorescent dye. The coverslips were mounted in PermaFluor (Immunotech). Localization of the proteins was examined using confocal laser microscopy (Leica).

Statistical Analysis

Experiments were usually performed in triplicate and repeated three times. The significance was evaluated by t-test or ANOVA at P<0.05, 0.01 or 0.001.

Results

Inhibition of LPS-induced iNOS Expression and Nitrite Formation in N9 Microglial Cells by TNL N9 microglial cells were stimulated with LPS in the absence or presence of TNL and Northern Blot was performed to analyse iNOS mRNA expression. FIG. 1A shows that the 4 kb iNOS mRNA species was equally induced at 4 and 8 hr after LPS stimulation. This induction was unaffected by the pretreatment (1 hr) with TNL. In contrast, 16 hr after activation with LPS, there was no further increase of iNOS mRNA in TNL-treated cells as opposed to vehicle-treated cells (FIG. 1B). Immunoblot analysis showed a time-dependent accumulation of the 130 kDa iNOS protein in N9 microglial cells after stimulation with LPS which was suppressed by TNL. DEX, a known inhibitor of iNOS expression (Minghetti, L., Nicolini, A., Polazzi, E., Greco, A., Perretti, M., Parente, L. and Levi, G. Br J Pharmacol 126(6):1307-1314, 1999), was used as a positive control (FIG. 1C). Next, nitrite formation from NO was assayed in the supernatant of LPS-stimulated N9 cells. While unstimulated N9 cells did not release NO (not shown), stimulation with LPS led to the production of nitrite. Treatment with TNL and DEX resulted in a concentration-dependent decrease in nitrite formation (FIG. 1D).

No Interference with LPS-induced Activation of NF-κB in N9 Microglial Cells by TNL NF-κB is a major transcriptional activator of iNOS in microglial cells (Xie, Q. J Biol Chem 272(23):14867-14872, 1997). In contrast to IFN-γ-stimulated N9 cells (Platten, M. et al. 2001 supra), TNL did not suppress the LPS-mediated phosphorylation of inhibitory-κB (I-κB) (FIG. 2A) and the subsequent generation of NF-κB reporter gene activity in N9 cells (FIG. 2B). When N9 cells were exposed to the NF-κB inhibitor BAY, a decrease of LPS-stimulated NO release was observed at 20 µM (11.1±0.7 µM/$10^4$ cells/48 hr vs. 14.6±1.0 µM/$10^4$ cells/48 hr in vehicle-treated cells).

TNL Inhibits the Phosphorylation of ERK-1/2, but not p38 MAPK in N9 Microglial Cells The mitogen-activated protein kinase (MAPK) signalling cascade—in particular p38MAPK and p44/42MAPK/extracellular signal-regulated kinase-1/2 (ERK-1/2)—has been implicated in the regulation of iNOS in LPS-activated microglial cells (Bhat, N. R., Zhang, P., Lee, J. C. and Hogan, E. L. J Neuosci 18(5):1633-1644, 1998). Therefore, we sought to investigate whether TNL interferes with the MAPK signalling pathway. Immunoblot analysis using phospho-specific antibodies demonstrated that the activation of N9 cells with LPS for 10 min resulted in the phosphorylation of p38 MAPK and p44/42 (ERK-1/2). Treatment with TNL led to a concentration-dependent inhibition of ERK-2 phosphorylation while phospho-ERK-1 and unphosphorylated ERK-1/2 protein levels remained unchanged (FIG. 3A). Densitometry revealed that phospho-ERK-2 was reduced by 80% after exposure to 300 µM TNL (FIG. 3B). TNL did not alter cellular phospho-p38 levels after LPS stimulation indicating that TNL specifically suppresses iNOS activation via inhibition of ERK-2 phosphorylation (FIG. 3A). Exposure of N9 cells to the MAPK/ERK kinase-1/2 (MEK-1/2) inhibitor PD which acts upstream of ERK-1/2 resulted in a significant inhibition of LPS-mediated nitrite formation (10.7±0.4 µM/$10^4$ cells/48 hr at 40 µM PD vs. 16.6±0.3 µM/$10^4$ cells/48 hr compared to vehicle-treated cells). Since PKC phosphorylates RAF, which acts directly upstream of MEK (Sozeri, O., Vollner, K., Liyanage, M., Frith, D., Kour, G., Mark JR., G. E. and Stabel, S. Oncogene 7(11):2259-2262, 1992) and since LPS-induced ERK-1/2 activation may be mediated by PKC (Chen, C. C. and Wang, J. K. Mol Pharmacol 55(3):481-488, 1999), we reasoned that PKC may be involved in LPS-mediated phosphorylation of ERK-1/2 in N9 cells. Long-term treatment (24 hr) with PMA depletes PKC in various cell types including micro glial (Kang, J., Yang, M., Jou, I. and Joe, E. Neurosci Lett 299(3):205-208, 2001). Immunoblot analysis demonstrated that PKCδ was effectively depleted in N9 cells after 24 hr treatment with PMA (100 nM, data not shown). While stimulation with LPS resulted in a rapid (10 min) phosphorylation of ERK-1/2, LPS failed to induce ERK-1/2 phosphorylation in N9 cells after prolonged pretreatment with PMA, indicating that PKC is required for LPS-mediated phosphorylation of ERK-1/2 in N9 microglial cells (FIG. 3C).

Figure 4:
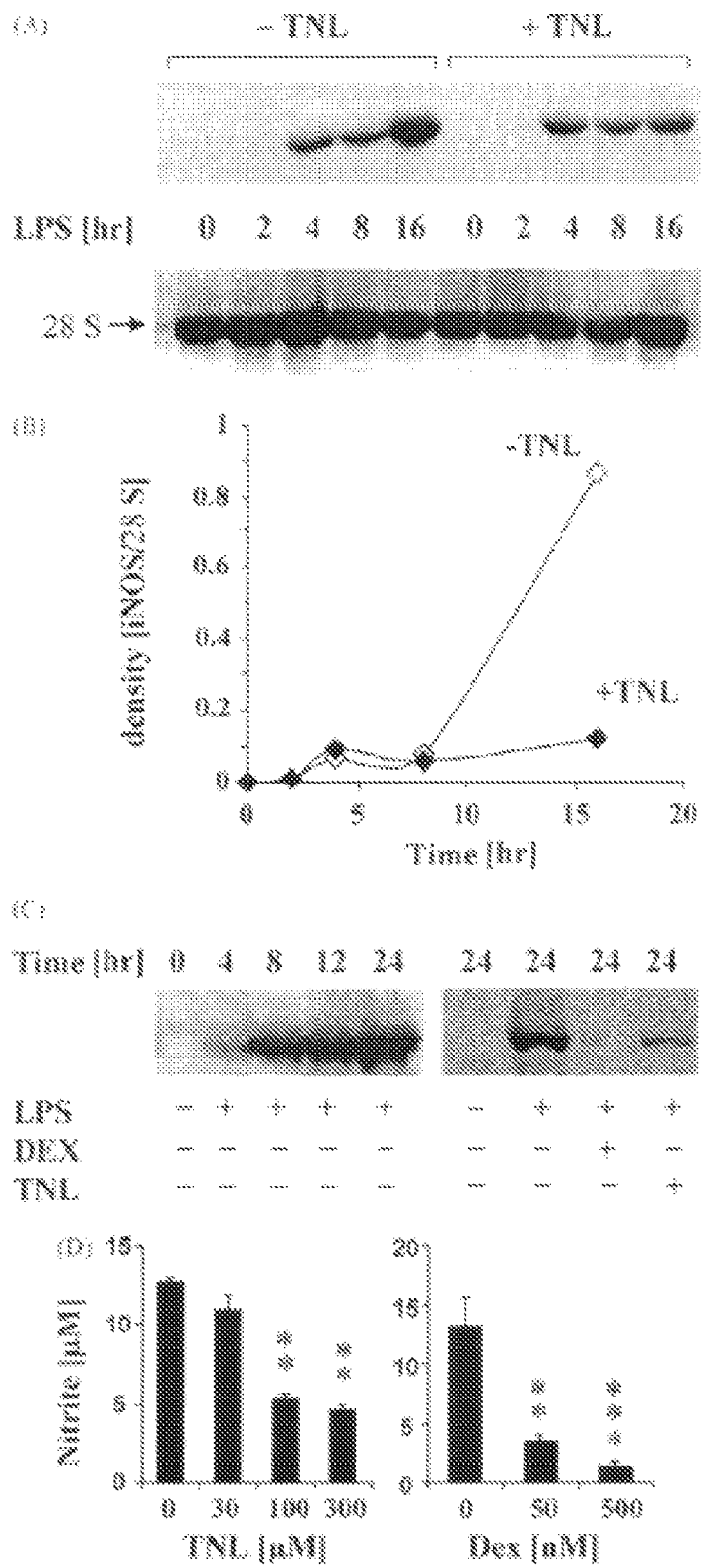
FIG. 4 is an image depicting that TNL inhibits microglial iNOS expression and NO release. (A) N9 cells were pretreated with vehicle (−TNL) or TNL (+TNL, 300 µM) for 1 hr and stimulated with LPS (10 µg/mL) for the time indicated. iNOS mRNA expression was examined by Northern blot of total RNA (5 µg per lane). Equal loading was ascertained by ethidium bromide staining of the 28S ribosomal fractions. (B) Densitometry of iNOS mRNA and 28S ribosomal RNA signals. Values are given as ratios of the densities of iNOS and 28S signals. Data are representative of two independent experiments. (C) N9 cells were exposed to vehicle or DEX (500 nM) or TNL (300 µM) and stimulated with LPS (10 µg/mL) for the time indicated. iNOS protein expression was examined by immunoblot of whole cell protein (20 µg per lane). Data are representative of three independent experiments. (D) N9 cells were stimulated with LPS alone (10 µg/mL) or in combination with TNL or DEX. Supernatant was collected after 48 hr and nitrite was measured using the Griess assay. Values expressed as $NO_2$ accumulated per $10^4$ cells (mean and SEM, N=3, P<0.01, *P<0.001, ANOVA).

Promotion of LPS-induced iNOS Expression and Nitrite Formation in N9 Microglial Cells by PKC We next analysed the role of PKC in LPS-mediated activation of N9 cells. Pretreatment (15 min) of N9 cells with PMA led to a superinduction of LPS-mediated iNOS protein expression and nitrite formation. Activation of PKC by PMA in the absence of LPS, however, did not induce iNOS protein expression (FIG. 4A). The depletion of PKC after 24-hr exposure to PMA (100 nM) resulted in a reduction of iNOS protein expression in response to LPS for 24 hr (FIG. 4B). Densitometry revealed that iNOS protein was reduced by 80% after 24-hr exposure to PMA (FIG. 4C).

Inhibition of PKCδ-Activation in N9 Microglial Cells by TNL

Figure 5:
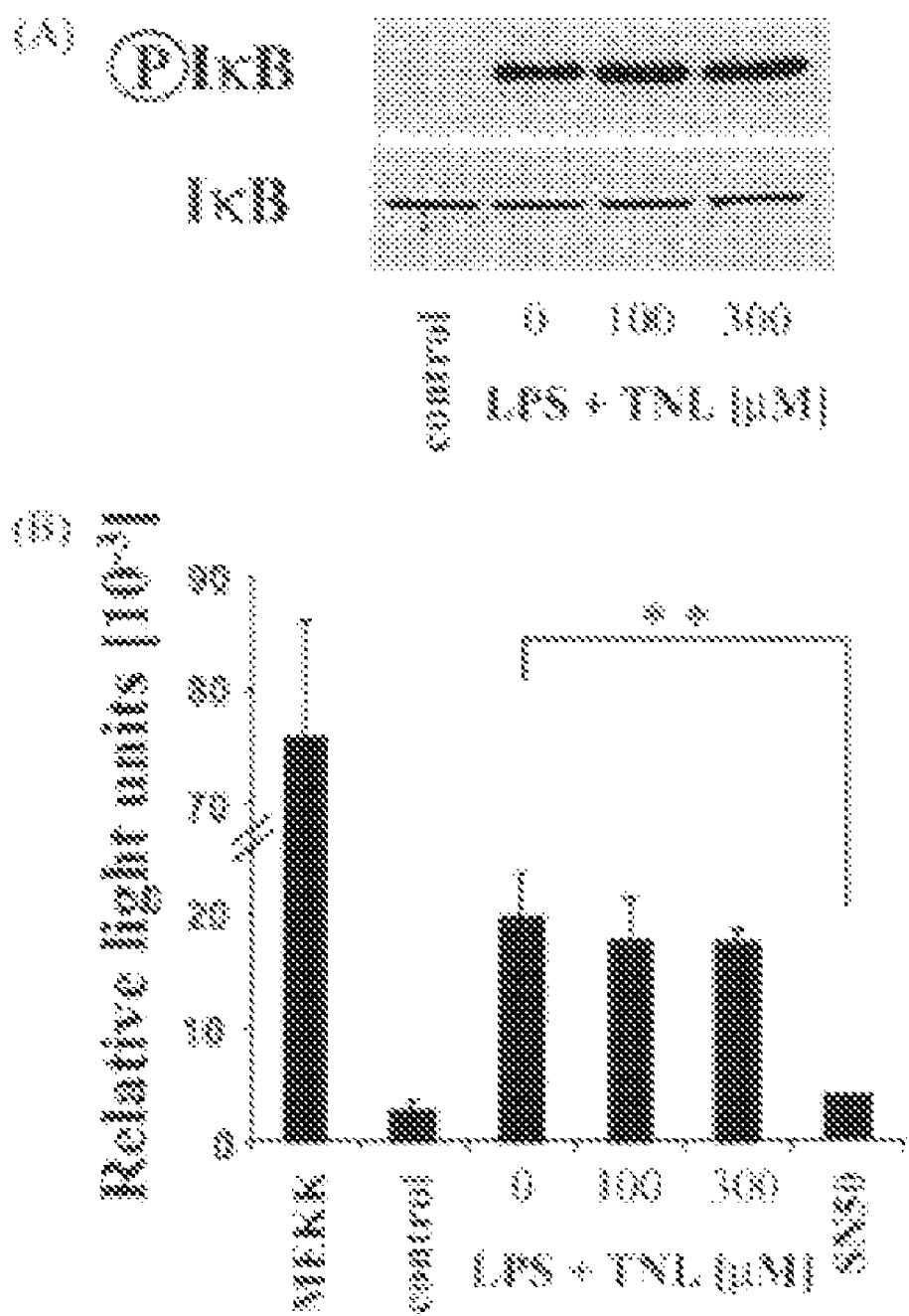
FIG. 5 is an image depicting that TNL does not interfere with LPS-induced activation of NF-κB. (A) N9 cells were left untreated or incubated with LPS (10 mg/mL) with or without pre-incubation (1 hr) with TNL at the concentrations indicated. Whole cell protein was prepared 1 hr after stimulation and subjected to immunoblot using an antiphospho IκBα antibody revealing a band at the predicted size (40 kDa). Equal IκBα-expression was ascertained by rehybridizing the membrane using a nonphospho-specific anti-IκBα antibody. Data re representative of two independent experiments. (B) In parallel, N9 cells were transiently transfected with an NF-κB reporter plasmid. At 24 hr after transfection cells were stimulated with LPS (10 µg/mL) for 4 hr with or without pre-incubation (1 hr) with NF-κB SN50 inhibitory peptide (SN50, 10 µg/mL) or TNL at the concentrations indicated. Transfection with a MEKK plasmid served as positive control for NFκB activation. Luciferase activity was determined by luminometry. Values are expressed as relative light units (RLU, mean and SEM, N=3, **P<0.01, t-test).
Figure 6:
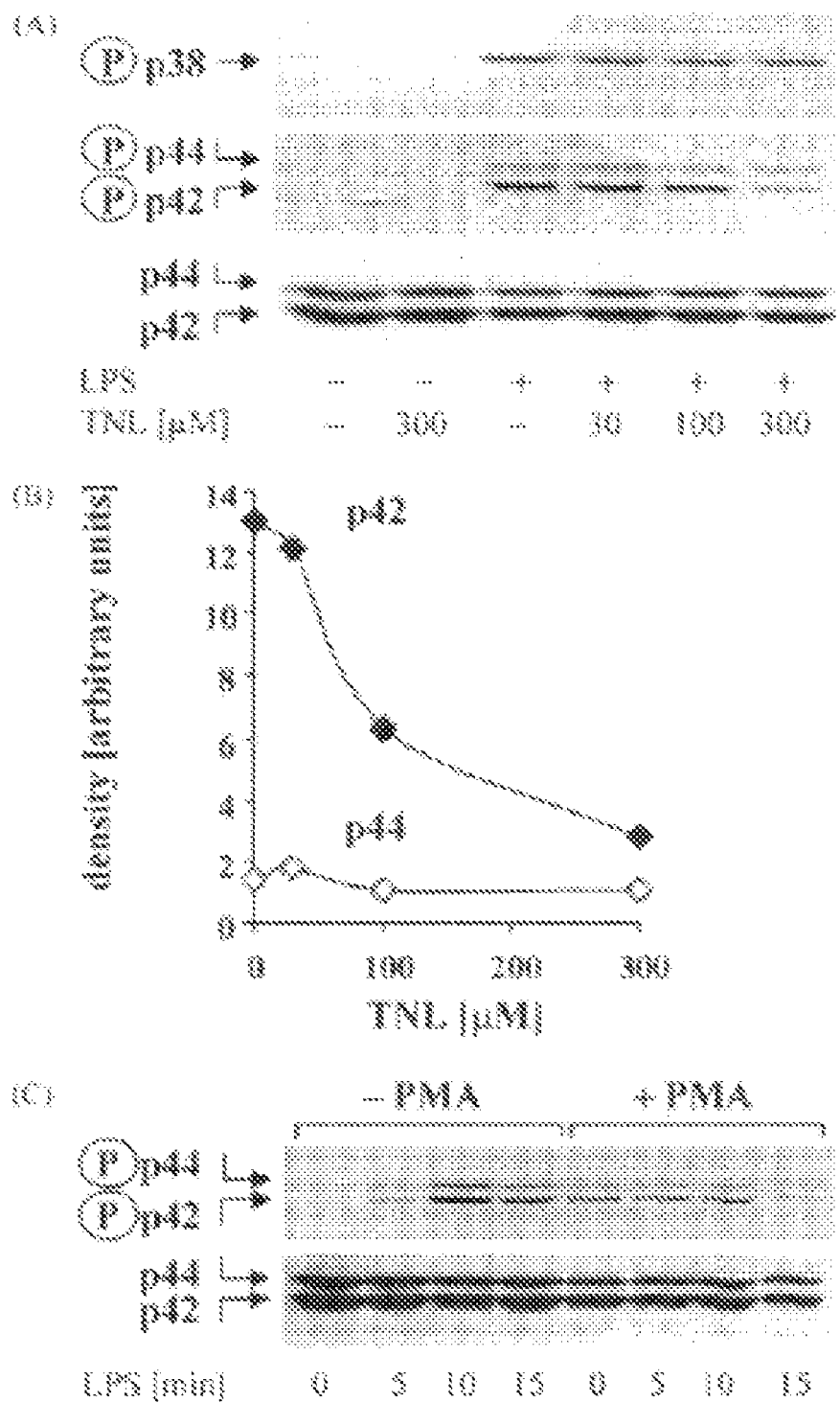
FIG. 6 is an image depicting that TNL suppresses LPS-stimulated phosphorylation of ERK-2. (A) N9 cells were stimulated with LPS (10 µg/mL) for 10 min with or without pre-incubation (1 hr) with TNL. Whole cell protein was subjected to immunoblot using antiphospho-p38 or antiphospho-ERK-1/2 antibodies. Equal ERK-1/2-expression was ascertained by re-hybridizing the membrane using a nonphospho-specific anti-ERK-1/2 antibody. Data are representative of three independent experiments. (B) Densitometry of the phospho-ERK-1/2 protein signals. Values are given as arbitrary units. (C) For depletion of PKC, N9 cells were long-term exposed to PMA (100 nM) for 24 hr and stimulated with LPS (10 µg/mL) for the time indicated. Whole cell protein was subjected to immunoblot using antiphospho-ERK-1/2 antibody. Equal ERK-1/2-expression was ascertained by re-hybridizing the membrane with a nonphospho-specific anti-ERK-1/2-antibody. Data are representative of three independent experiments.
Figure 7:
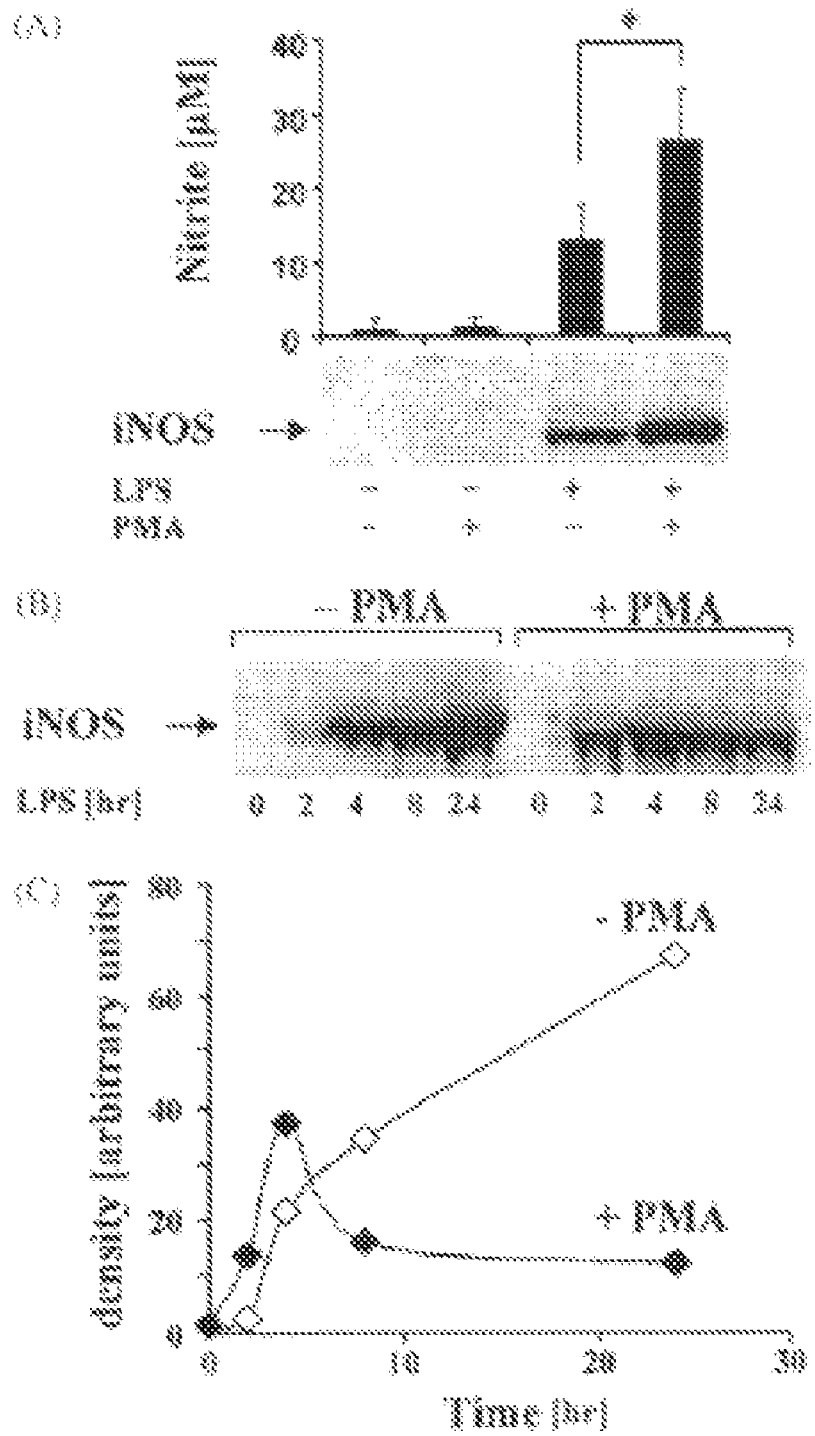
FIG. 7 is an image depicting that PKC promotes LPS-induced iNOS expression and nitrite formation. (A) N9 cells were untreated or stimulated with LLPS (10 µg/mL) without or with short-term pre-incubation (15 min) with PMA (100 nM). Supernatant was collected after 48 hr and nitrite was measured using the Griess assay (upper panel). Values are expressed as $NO_2$ accumulated per $10^4$ cells (mean and SEM, N=3, *P<0.05, t-test). In parallel, iNOS protein levels were examined 24 hr after stimulation (lower panel). Data are representative of three independent experiments. (B) N9 cells were stimulated with LLPS (10 µg/mL) without or with pre-exposure to PMA (100 nM) for 24 hr. iNOS protein levels were examined at the indicated time points by immunoblot. (C) Densitometry of the iNOS protein signals. Values are given as arbitrary units. Data are representative of three independent experiments.
Figure 8:
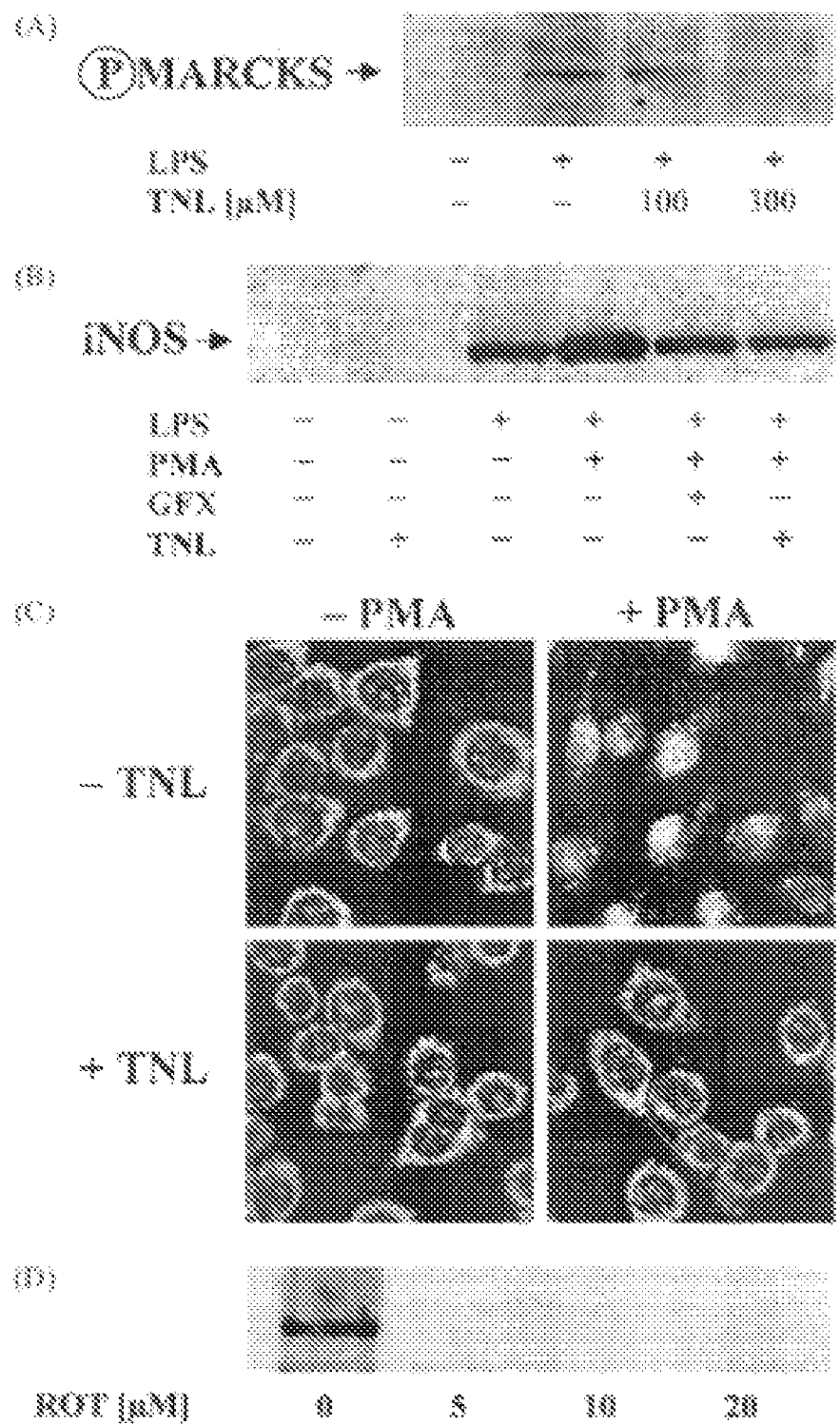
FIG. 8 is an image depicting that TNL inhibits the activation of PKCδ. (A) N9 cells were stimulated with LPS (10 µg/mL) for 1 hr without or with pre-incubation (1 hr) with TNL at the concentrations indicated. MARCKS phosphorylation was examined by immunoblot using a phospho-specific anti-MARCKS antibody. Data are representative of three independent experiments. (B) N9 cells were untreated or stimulated with LPS (10 µg/mL) for 24 hr without or with prior activation of PKC by short-term exposure to PMA (100 nM) for 15 min in the absence or prescence of TNL (300 µM) or GFX (2 µM). iNOS protein levels were assessed by immunoblot 24 hr after treatment. Data are representative of three independent experiments. (C) N9 cells were grown on coverslips and stimulated with PMA (100 nM) for 25 min without or with pre-incubation with TNL (300 µM). Cellular distribution of PKCδ was examined by immunocytochemistry. Data are representative of three independent experiments. (D) N9 cells were stimulated with LLPS (10 µg/mL) for 24 hr without or with co-incubation with ROT at the concentrations indicated. iNOS protein levels were examined by immunoblot. Data are representative of three independent experiments.

We then tested the hypothesis that TNL inhibits LPS-induced iNOS activation by inhibition of PKC. Immunoblot analysis using a phospho-specific antibody demonstrated that the phosphorylation of the PKCδ substrate, MARCKS) is induced by short-term treatment with LPS. MARCKS phosphorylation was inhibited when PMA-activated N9 cells were co-exposed to TNL, supporting the notion that TNL inhibits PKC in N9 cells (FIG. 5A). Moreover, while short-term treatment with PMA super-induced iNOS protein levels in LPS-stimulated N9 cells, this superinduction was abolished by co-exposure to either the PKC inhibitor GFX or TNL (FIG. 5B). Since PKCδ appears to be a specific kinase of ERK-1/2 (Ueda, Y., Hirai, S., Osaka, S., Suzuki, A., Mizuno, K. and Ohno, S. J Biol Chem 271(38):23512-23519, 1996), we tested the hypothesis that PKCδ is involved in LPS-mediated iNOS activation in N9 cells. PKCδ is confined to the cytosol in resting cells but rapidly translocates to particulate fractions after activation by short-term treatment with PMA (Wang, Q. J., Bhattacharyya, D., Garfield, S., Nacro, K., Marquez, V. E.

and Blumberg, P. M. *J Biol Chem* 274(52):37233-37239, 1999). Immunocytochemistry showed that PKCδ translocates from the cytosol primarily to the nucleus following exposure to PMA (100 nM) for 15 min. Co-exposure to TNL abolished this translocation of PKCδ (FIG. 5C). In addition, ROT which at low micromolar concentrations primarily inhibits the nonclassical δ-isoform of PKC (Gschwentd, M., Muller, H. J., Kielbassa, K., Zang, R., Kittlstein, W., Rincke, G. and Marks, F. *Biochem Biosphys Res Commun* 199(1):93-98, 1994), strongly inhibited iNOS protein accumulation in LPS-stimulated N9 cells at concentrations as low as 5 μM (FIG. 5D).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Beckman, J. S., Beckman, T. W., Chen, J., Marshall, P. A. and Freeman, B. A., *Prac. Natl. Acad. Sci. USA.*, 87:1620-1624, 1990.

Bhat, N. R., Zhang, P., Lee, J. C. and Hogan, E. L. *J Neuosci* 18(5):1633-1644, 1998.

Chabrier, P. E., Demerle-Pallardy, C. and Auguet, M. *Cell. Molecule. Life Sci.*, 55: 1029-1035, 1999.

Chen, C. C. and Wang, J. K. *Mol Pharmacol* 55(3):481-488, 1999.

Galea, E., Feinstein, D. L. and Reis, D. J. *Proc. Natl. Acad. Sci. USA.*, 89:10945-10949, 1992.

Gonzalez-Scarano, F. and Baltuch, G. *Annu Rev Neurosci*, 22:219-240, 1999.

Green, L. C., Wagner, D. A., Glogowski, J., Skipper, P. L., Wishnok, J. S. and Tannenbaum, S. R. *Anal Biochem* 126 (1):131-138, 1982.

Griffith, O. W. and Stuehr, D. J. *Annu Rev Physiol.*, 5:707-736, 1995.

Green, L. C., Wagner, D. A., Glogowski, J., Skipper, P. I., Wishnok, J. S. and Tannenbaum, S. R. *Anal. Biochem.*, 126:131-138, 1982.

Gschwentd, M., Muller, H. J., Kielbassa, K., Zang, R., Kittlstein, W., Rincke, G. and Marks, F. *Biochem Biosphys Res Commun* 199(1):93-98, 1994.

Hu, S., Sheno, W. S., Peterson, P. K. and Chao, C. C. *Glia.*, 15:491-494, 1995.

Kang, J., Yang, M., Jou, I. and Joe, E. *Neurosci Lett* 299(3): 205-208, 2001.

Minghetti, L., Nicolini, A., Polazzi, E., Greco, A., Perretti, M., Parente, L. and Levi, G. *Br J Pharmacol* 126(6):1307-1314, 1999.

Nathan, C. *FASEB. J*, 6:3051-3064, 1992.

Nathan, C. and Xie, Q. W. *J. Biol. Chem.*, 269:13725-13728, 1994.

Platten, M., Wild-Bode, C., Wick, W., Leitlein, J., Dichgans, J. and Weller, M. *Int. J. Cancer*, 93:53-61, 2001.

Platten, M., Wick, W., Wischhusen, J. and Weller, M. *Br J Pharmacol* 134(6):1279-1284, 2001.

Rieger, J., Stander, M., Loschmann, P. A., Heneka, M., Dichgans, J., Klockgether, T. and Weller, M. *Oncogene*, 17:2323-2332, 1998.

Righi, M., Mori, L., De Libero, G., Sironi, M., Biondi, A., Mantovani, A., Donini, S. D. and Ricciardi-Castagnoli, P. *Eur J Immunol* 19(8):1443-1448, 1989.

Sozeri, O., Vollmer, K., Liyanage, M., Frith, D., Kour, G., Mark JR., G. E. and Stabel, S. *Oncogene* 7(11):2259-2262, 1992.

Ueda, Y., Hirai, S., Osaka, S., Suzuki, A., Mizuno, K. and Ohno, S. *J Biol Chem* 271(38):23512-23519, 1996.

Wang, Q. J., Bhattacharyya, D., Garfield, S., Nacro, K., Marquez, V. E. and Blumberg, P. M. *J Biol Chem* 274(52): 37233-37239, 1999.

Xie, Q. *J Biol Chem* 272(23):14867-14872, 1997.

The invention claimed is:

1. A method for the treatment of a condition in a mammal, said method comprising administering to said mammal an effective amount of tranilast or a pharmaceutically acceptable salt thereof, wherein said condition is multiple sclerosis.

2. The method of claim 1, wherein said administering is selected from a group consisting of administering respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip, patch and implant.

3. The method of claim 1, wherein said effective amount is from about 0.1 mg to about 1 mg per kilogram body weight per day of said mammal.

4. The method of claim 1, wherein said tranilast or pharmaceutically acceptable salt is administered orally.

5. The method of claim 1, wherein said administration is daily, weekly, or monthly.

6. The method of claim 1, wherein said effective amount is from about 0.1 µg to 2000 mg.

7. The method of claim 1, wherein said administering is via a tablet, troche, pill, capsule, syrup, suspension, wafer or elixir.

8. The method of claim 1, wherein said tranilast or a pharmaceutically acceptable salt thereof is present in a composition at least 1% by weight of said composition.

9. The method of claim 1, wherein said tranilast or a pharmaceutically acceptable salt thereof is present in a composition at about 5% to about 80% by weight of said composition.

* * * * *

UNITED STATES PATENT AND TRADEMARK OFFICE
CERTIFICATE OF CORRECTION

PATENT NO. : 7,531,575 B2  
APPLICATION NO. : 10/697655  
DATED : May 12, 2009  
INVENTOR(S) : Weller et al.

Page 1 of 1

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 1186 days.

Delete the phrase "by 1186 days" and insert -- by 1593 days --

Signed and Sealed this

Twentieth Day of April, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
aagctgcatg tgacatcgac                                               20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
atgtgtctgc agatgtgctg                                               20